US012569536B2

(12) United States Patent
Millward et al.

(10) Patent No.: US 12,569,536 B2
(45) Date of Patent: Mar. 10, 2026

(54) MACROCYCLIC PEPTIDES FOR TARGETED INHIBITION OF AUTOPHAGY

(71) Applicant: Board of Regents, The University of Texas System, Austin, TX (US)

(72) Inventors: Steven Millward, Houston, TX (US); Joshua Gray, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 333 days.

(21) Appl. No.: 17/425,546

(22) PCT Filed: Jan. 30, 2020

(86) PCT No.: PCT/US2020/015816
§ 371 (c)(1),
(2) Date: Jul. 23, 2021

(87) PCT Pub. No.: WO2020/160221
PCT Pub. Date: Aug. 6, 2020

(65) Prior Publication Data
US 2022/0096594 A1     Mar. 31, 2022

Related U.S. Application Data

(60) Provisional application No. 62/799,388, filed on Jan. 31, 2019.

(51) Int. Cl.
| | |
|---|---|
| *A61K 38/12* | (2006.01) |
| *A61K 31/282* | (2006.01) |
| *A61K 33/243* | (2019.01) |
| *A61K 45/06* | (2006.01) |
| *A61K 49/00* | (2006.01) |
| *A61P 35/00* | (2006.01) |

(52) U.S. Cl.
CPC ............ *A61K 38/12* (2013.01); *A61K 31/282* (2013.01); *A61K 33/243* (2019.01); *A61K 45/06* (2013.01); *A61K 49/0056* (2013.01); *A61P 35/00* (2018.01)

(58) Field of Classification Search
CPC .... A61K 38/12; A61K 31/282; A61K 33/243; A61K 45/06; A61K 49/0056; A61K 38/00; A61P 35/00; C07K 7/56
See application file for complete search history.

(56) References Cited

U.S. PATENT DOCUMENTS 7,504,490 B1     3/2009   Weinstock et al.

OTHER PUBLICATIONS

Bowie et al (Science, 1990, 247:1306-1310) (Year: 1990).*
Burgess et al (J. Cell Biol. 111:2129-2138, 1990) (Year: 1990).*

Lazar et al (Mol. Cell. Biol., 8:1247-1252, 1988) (Year: 1988).*
Alemu et al., "ATG8 family proteins act as scaffolds for assembly of the ULK complex: sequence requirements for LC3-interacting region (LIR) motifs," *J. Biol. Chem.*, 2012.
Birgisdottir et al., "The LIR motif—crucial for selective autophagy," *Journal of Cell Science*, 126:3237-3247, 2013.
Fiacco et al., "Directed evolution of scanning unnatural protease resistant (SUPR) peptides for in vivo applications," Chembiochem., 17:1643-1651, 2016.
Galan-Cobo et al., "LKB1 deficiency and KEAP1/NRF2 pathway alterations as biomarkers of response for ATR and ATM inhibitors and other inhibitors of DNA damage response (DDR) in NSCLC," Abstract A096, In: Proceedings of the AACR-NCI-EORTC International Conference on Molecular Targets and Cancer Therapeutics; Oct. 26-30, 2019; Boston, MA. Philadelphia (PA): AACR; *Mol Cancer Ther.*, 18(12 Suppl), 2019.
Gray et al., "Directed evolution of imaging agents and therapeutics targeting LC3 and autophagy," Abstract, Third AACR-SNMMI Joint Conference on State-of-the-Art Molecular Imaging in Cancer Biology and Therapy: Abstracts, 2018.
Gray et al., "Directed evolution of imaging agents and therapeutics targeting LC3 and autophagy," Poster, Third AACR-SNMMI Joint Conference on State-of-the-Art Molecular Imaging in Cancer Biology and Therapy, 2018.
Jacomin et al., "iLIR database: a web resource for LIR motif-containing proteins in eukaryotes," *Autophagy*, 12(10):1945-1953, 2016.
Keown et al., "A helical LC3-interacting region mediates the interaction between the retroviral restriction factor Trim5α and mammalian autophagy-related ATG8 proteins," *J. Biol. Chem.*, 293(47):18378-18386, 2018.
Lee et al., "Development of LC3/GABARAP sensors containing a LIR and a hydrophobic domain to monitor autophagy," *The EMBO Journal*, 36(8):1100-1116, 2017.
PCT International Preliminary Report on Patentability issued in International Application No. PCT/US2020/015816, mailed Aug. 12, 2021.
PCT International Search Report and Written Opinion issued in International Application No. PCT/US2020/015816, mailed Jul. 16, 2020.
Popelka et al., "Analysis of the native conformation of the LIR/AIM motif in the Atg8/LC3/GABARAP-binding proteins," *Autophagy*, 11(12):2153-2159, 2015.
Song et al., "Natural cyclopeptide RA-XII, a new autophagy inhibitor, suppresses protective autophagy for enhancing apoptosis through AMPK/mTOR/P70S6K pathways in HepG2 cells," *Molecules*, 22:1934, 2017.
Stolz et al., "Fluorescence-based ATG8 sensors monitor localization and function of LC3/GABARAP proteins," *The EMBO Journal*, 36:549-564, 2017.

* cited by examiner

*Primary Examiner* — Sudhakar Katakam
(74) *Attorney, Agent, or Firm* — pH IP Law

(57)                    ABSTRACT

Provided herein are cyclic peptide inhibitors of autophagy that bind to LC3. These cyclic peptides may be used to treat diseases or disorders associated with autophagy, such as, for example, cancer, diabetes, cardiovascular disease, and neurological disorders. These cyclic peptides may also be used to sensitize cancers to front-line chemotherapy, immunotherapy, and/or radiation therapy.

10 Claims, 23 Drawing Sheets
Specification includes a Sequence Listing.

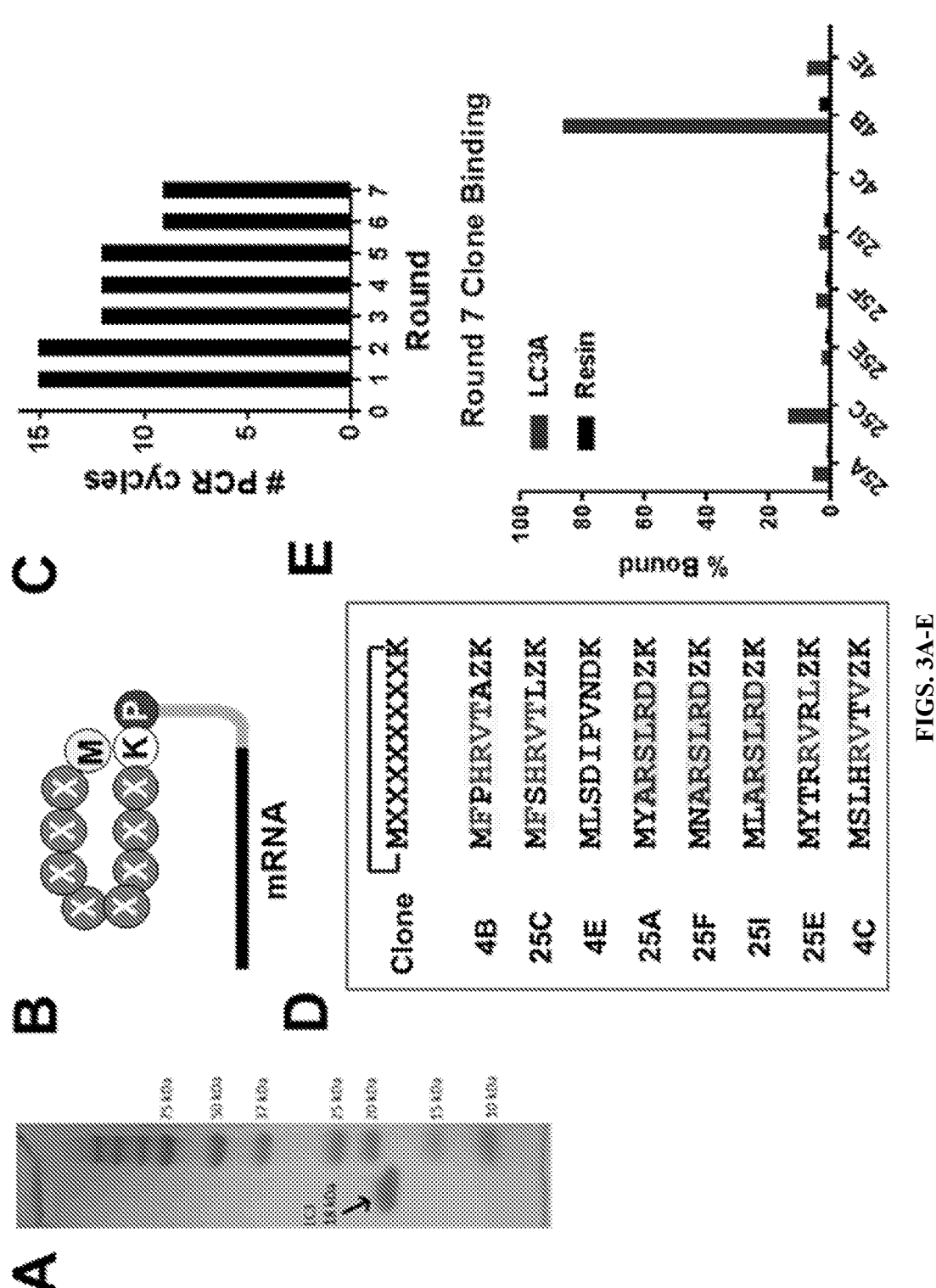
FIGS. 3A-E

FIG. 5A

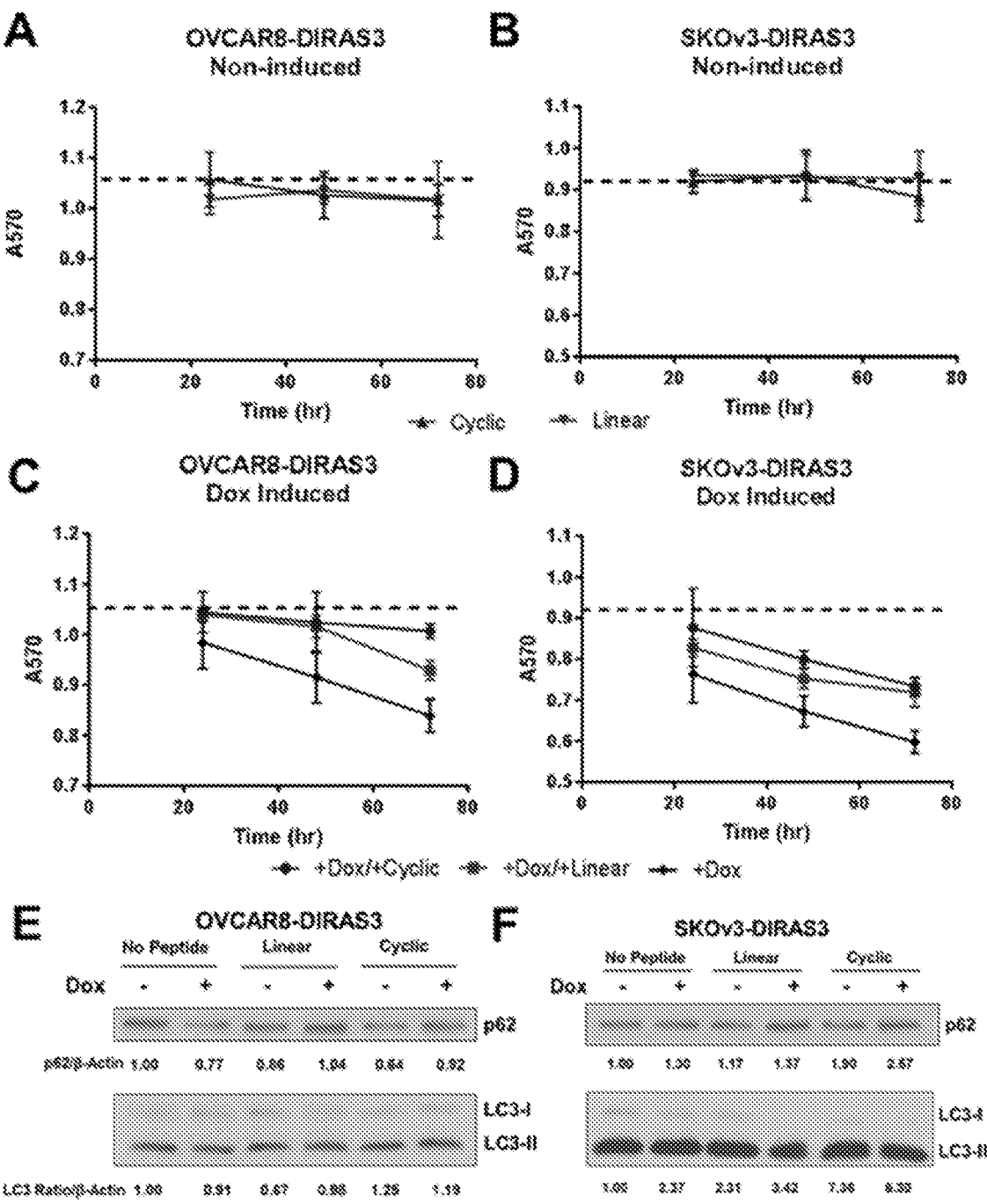
FIGS. 8A-F

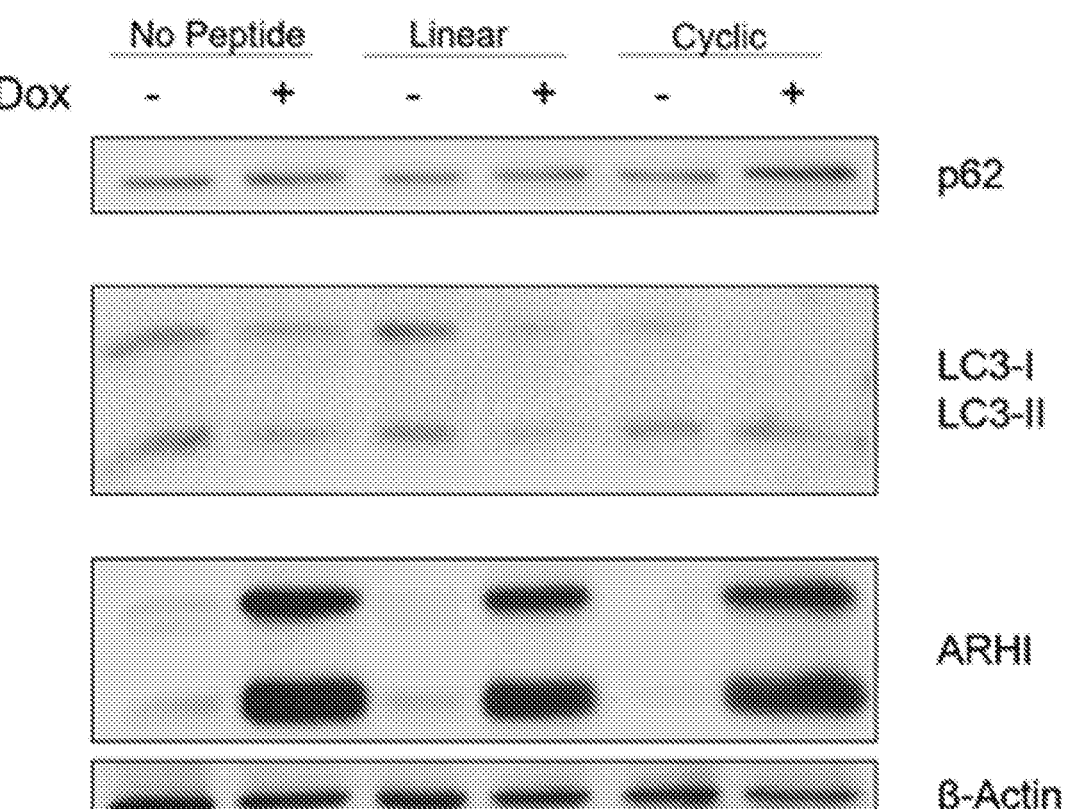
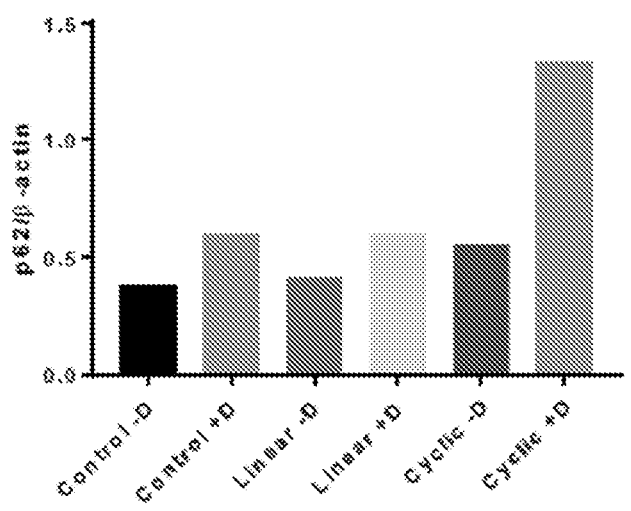
FIG. 10B

OVCAR8-ARHI (72hr)
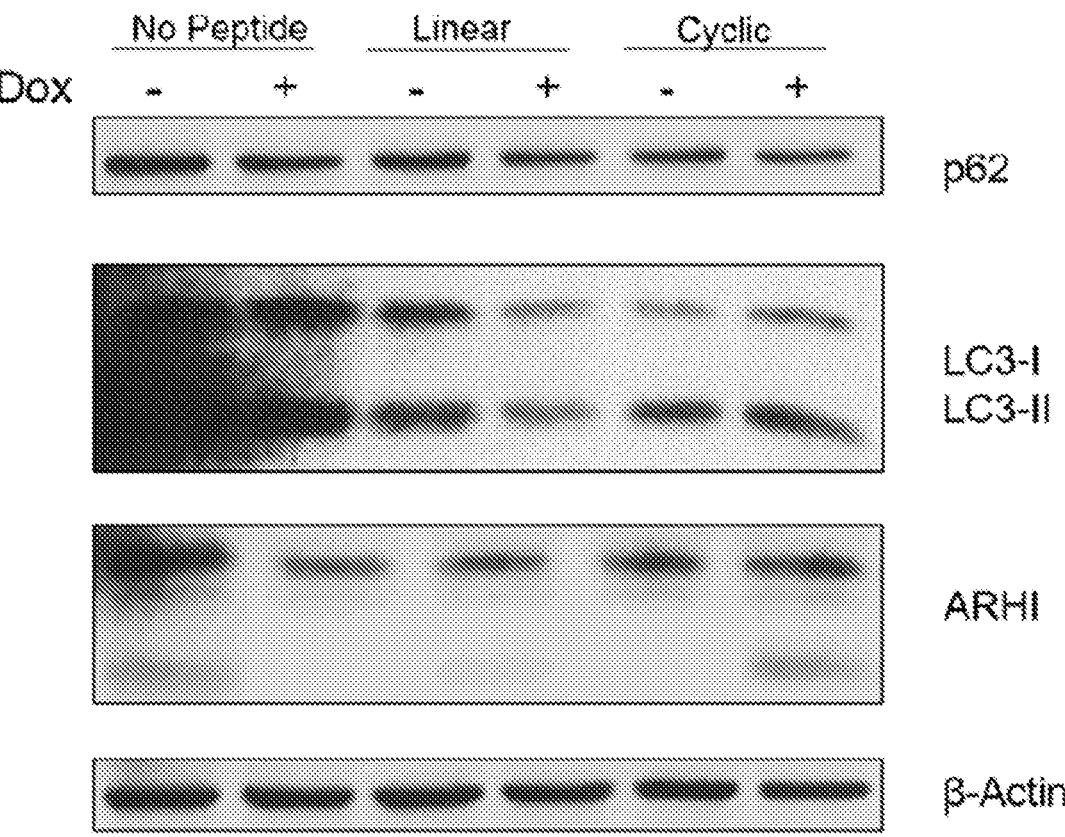
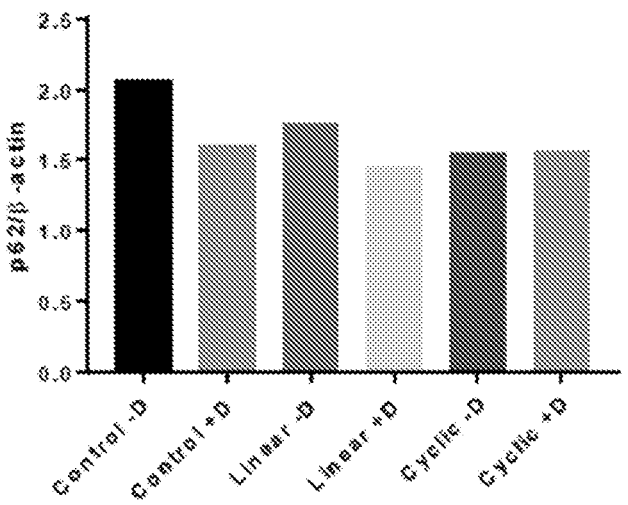
FIG. 10C

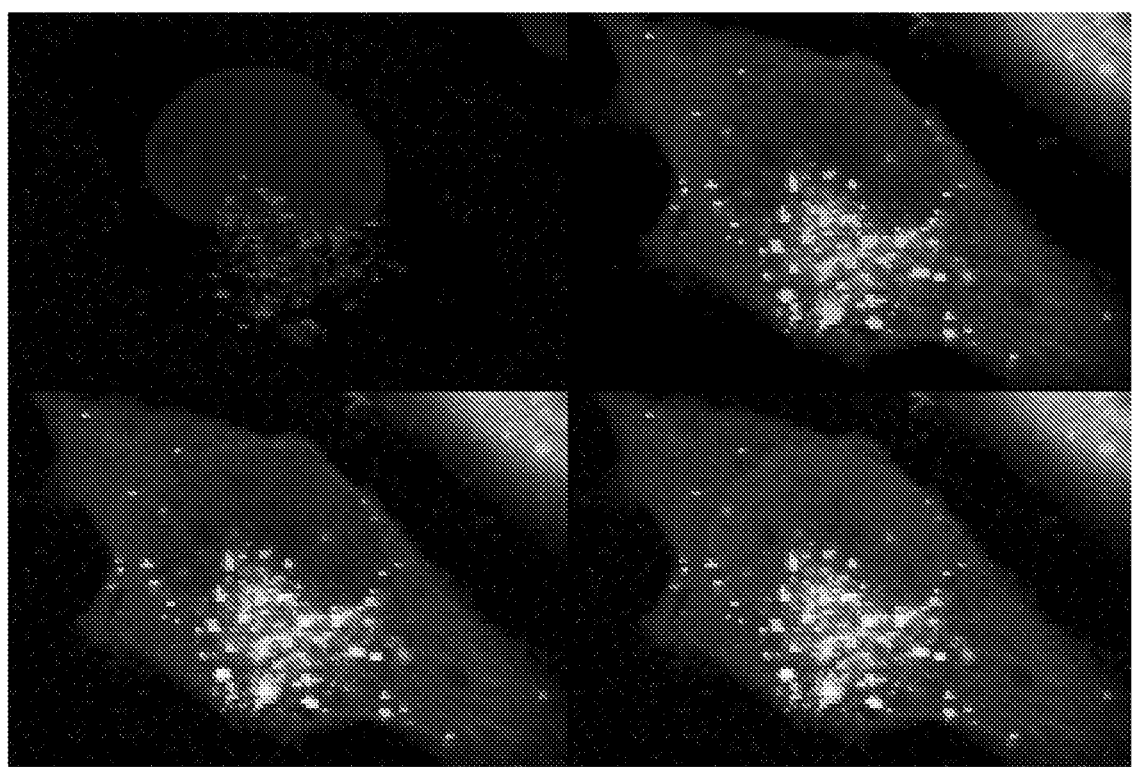
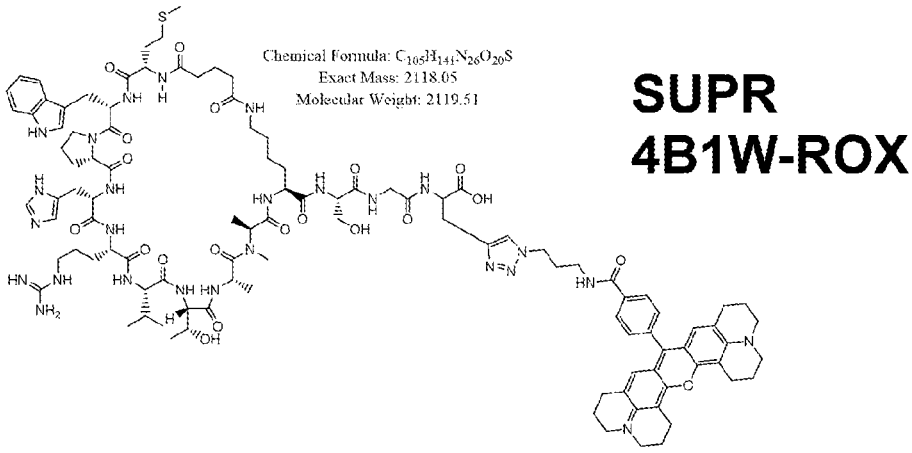
Chemical Formula: C₁₀₅H₁₄₁N₂₆O₂₀S
Exact Mass: 2118.05
Molecular Weight: 2119.51
**SUPR
4B1W-ROX**
FIG. 11

FIGS. 12A-D

MACROCYCLIC PEPTIDES FOR TARGETED INHIBITION OF AUTOPHAGY

REFERENCE TO RELATED APPLICATIONS

The present application is a national phase application under 35 U.S.C. § 371 of International Application No. PCT/US2020/015816, filed Jan. 30, 2020, which claims the priority benefit of U.S. provisional application No. 62/799,388, filed Jan. 31, 2019, the entire contents of each of which are incorporated herein by reference.

STATEMENT REGARDING FEDERALLY SPONSORED RESEARCH

This invention was made with government support under Grant No. R21 CA181994 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Sep. 17, 2024, is named UTSCP1425US_ST25.txt and is 4,860 bytes in size.

BACKGROUND

1. Field

The present disclosure relates generally to the field of medicine. More particularly, it concerns cyclic peptide inhibitors of LC3 and methods of their use.

2. Description of Related Art

Autophagy is a homeostatic cellular recycling process that is highly conserved among eukaryotes from yeast to mammals in order to survive temporary periods of cellular stress such as nutrient deprivation. Upon induction of autophagy, damaged proteins and organelles in the cytosol are sequestered inside double-membraned vesicles called autophagosomes and are subsequently shepherded to the lysosome where they are degraded to basic metabolites. Dysregulation of autophagy has been observed in a variety of cancer types both as a mechanism to avoid programmed cell death and enter dormancy, as a means to survive the hypoxic and nutrient deprived conditions often found in the developing tumor microenvironment, and to mediate resistance to standard treatment techniques such as chemotherapy and radiation. Since autophagy in the context of cancer typically involves prolonged activation of what is normally a temporary stress-response mechanism, it presents a promising target for enhancing the effects of front-line therapies without seriously impacting normal tissue that should not be dependent on autophagy for survival. For these reasons, interest in autophagy inhibitors for use with gold-standard treatment methods has increased dramatically over the last fifteen years. As of 2018, over 30 Phase I and Phase II clinical trials in the US combining chloroquine (CQ) and hydroxychloroquine (HCQ)—the only autophagy inhibitors currently in clinical use—with chemotherapy or radiation are underway or have already completed. Unfortunately, these compounds have serious drawbacks as they are non-specific, untargeted lysosomotropic agents that affect lysosomal pH rather than the autophagic machinery itself. Because of this, CQ & HCQ have generally shown poor efficacy, unfavorable pharmacokinetics, and high normal-tissue toxicity due to the disruption of essential cellular processes. As such, targeted inhibitors of autophagy are needed.

SUMMARY

Provided herein are macrocyclic peptides that bind to a functional site on LC3. The provided peptides are cell-permeable, engage LC3 inside the cell, and inhibit LC3-mediated protein-protein interactions. This results in inhibition of autophagosome elongation/maturation and autophagic flux. Labeling these peptides with a fluorophore (e.g., fluorescein or rhodamine) can be used to generate molecular imaging probes to visualize autophagosomes in living cells.

In one embodiment, provided herein are cyclic peptide autophagy inhibitors comprising a sequence at least 90% identical to a peptide sequence of any one of SEQ ID NOs: 1-9. In some aspects, the lysine residue at position 10 is cyclized to the N-terminus of the peptide. In some aspects, the N-terminal amino group of the peptide is crosslinked with the side chain of the lysine at position 10 using a di-succinimidyl glutarate crosslinker. In some aspects, the peptide comprises D amino acids. In some aspects, the peptide comprises at least one N-methylated amino acid. In some aspects, the peptide comprises at least one N-methyl-alanine. In some aspects, the amino acid in position 9 is an N-methylalanine. In some aspects, the peptide is lipidated. In some aspects, the peptide is PEG-ylated. In some aspects, the peptide further comprises a detectable label. In some aspects, the peptide binds to LC3. In some aspects, the peptide is protease-resistant.

In one embodiment, provided herein are cyclic peptide autophagy inhibitors comprising the sequence of $MX_1X_2X_3RVX_4X_5ZK$-COOH (SEQ ID NO: 16), wherein $X_1$ is W, F, or Y; $X_2$ is P, S, or T; $X_3$ is H or R; $X_4$ is T or R; and $X_5$ is A or L, and wherein the side chain of Lys10 is bound to the N-terminus of the peptide. Z represents N-methylalanine. In some aspects, $X_1$ is W, $X_2$ is P, $X_3$ is H, $X_4$ is T, and $X_5$ is A. In some aspects, $X_1$ is F, $X_2$ is P, $X_3$ is H, $X_4$ is T, and $X_5$ is A. In some aspects, $X_1$ is F, $X_2$ is S, $X_3$ is H, $X_4$ is T, and $X_5$ is L. In some aspects, $X_1$ is Y, $X_2$ is T, $X_3$ is R, $X_4$ is R, and $X_5$ is L. In some aspects, the peptide is lipidated. In some aspects, the peptide is PEG-ylated. In some aspects, the peptide further comprises a detectable label. In some aspects, the peptide binds to LC3. In some aspects, the peptide is protease-resistant.

In one embodiment, provided herein are cyclic peptide autophagy inhibitors comprising the sequence of $MX_1ARSLRDZK$-COOH (SEQ ID NO: 17), wherein $X_1$ is Y, N, W, or L, and wherein the side chain of Lys10 is bound to the N-terminus of the peptide. Z represents N-methylalanine. In some aspects, $X_1$ is Y. In some aspects, $X_1$ is N. In some aspects, $X_1$ is L. In some aspects, $X_1$ is W. In some aspects, the peptide is lipidated. In some aspects, the peptide is PEG-ylated. In some aspects, the peptide further comprises a detectable label. In some aspects, the peptide binds to LC3. In some aspects, the peptide is protease-resistant.

In one embodiment, provided herein are pharmaceutical formulations comprising a cyclic peptide of any one of the present embodiments in a pharmaceutically acceptable carrier. In some aspects, the cyclic peptide is encapsulated or embedded in a delivery vehicle. In some aspects, the delivery vehicle is a liposome, a lysosome, a microcapsule or a nanoparticle. In some aspects, the pharmaceutical formulations further comprise a platinum-based chemotherapeutic agent. In some aspects, the pharmaceutical formulations further comprise an alkylating agent. In some aspects, the pharmaceutical formulations further comprise a cytotoxin. In some aspects, the pharmaceutical formulations further comprise an immune checkpoint inhibitor.

In one embodiment, provided herein are methods of treating a disease or disorder associated with autophagy in a patient in need thereof, the method comprising administering to the patient a formulation of any one of the present embodiments. In some aspects, the patient is a human. In some aspects, the formulation is administered intravenously, intradermally, intraarterially, intraperitoneally, intralesionally, intracranially, intraarticularly, intraprostatically, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

In some aspects, the disease or disorder is a cancer. In some aspects, the cancer is ovarian cancer or pancreatic cancer. In some aspects, the patient has been previously treated for cancer. In some aspects, the cancer is in remission. In some aspects, the formulation is administered as a chemopreventive. In some aspects, the methods further comprise administering to the subject a second anti-cancer agent. In some aspects, the second anti-cancer agent is a platinum-based chemotherapeutic agent, such as, for example, cisplatin, carboplatin, or oxaliplatin. In some aspects, the cancer has been determined to be resistant to a platinum-based chemotherapeutic agent, and the method sensitizes the cancer to treatment with a platinum-based chemotherapeutic agent. In some aspects, the second anti-cancer agent is radiation therapy. In some aspects, the cancer has been determined to be resistant to radiotherapy. In some aspects, the second anti-cancer agent is an immunotherapy, such as an immune checkpoint inhibitor. In some aspects, the method potentiates that activity of the immunotherapy.

In some aspects, the disease or disorder is neurodegeneration, inflammation, Crohn's disease, various myopathies, liver disease, or heart disease.

In one embodiment, provided herein is the use of a cyclic peptide of any one of the present embodiments for the treatment of a disease or disorder associated with autophagy in a patient. In one embodiment, provided herein is a cyclic peptide of any one of the present embodiments for use in the treatment of a disease or disorder associated with autophagy. In one embodiment, provided herein is a cyclic peptide of any one of the present embodiments for use in the manufacture of a medicament for the treatment of a disease or disorder associated with autophagy.

In one embodiment, provided herein are methods of visualizing autophagosome formation and/or autophagosome localization in living cells, the method comprising contacting living cells with a composition comprising a cyclic peptide of the present embodiments bound to a detectable label and detecting the location of the detectable label. In some aspects, the detectable label is a fluorescent label. In some aspects, the living cells are a cell culture, a primary cell culture, a tissue culture, a biopsy sample, or living cells with a living animal.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A—mRNA-peptide fusion formation. mRNA sequences are ligated to puromycin via a poly-adenine linker. During translation, puromycin enters the A site of the ribosome, resulting in a covalent link between the C-terminus of the growing peptide chain and its encoding mRNA, which induces premature detachment of the ribosome. The resulting mRNA-peptide fusions can be post-translationally cyclized and selected for function. FIG. 2B—SUPR mRNA display selection workflow. DNA libraries are transcribed into mRNA and ligated to a poly-dA-puromycin linker. The resulting templates are translated in rabbit reticulocyte lysate in the presence of an amber suppressor tRNA chemically charged with the unnatural amino acid, N-methylalanine. This results in the incorporation of N-methylalanine at stop codon positions. The resulting mRNA-peptide fusions are purified and cyclized through the addition of the bis-NHS cross-linker disuccinimidyl glutarate (DSG) to generate the MX8K library. This library is reverse-transcribed, treated with immobilized protease, and panned against immobilized LC3A. Sequences that bind tightly to LC3 are retained after washing while non-functional sequences are lost. PCR amplification of the bound library members generates the DNA library for the next round of selection. Alternatively, DNA sequencing can be carried out to identify the amino acid sequences of the functional peptides.

FIGS. 3A-E: LC3 SUPR mRNA Display Selections. Design and results. FIG. 3A—SDS-PAGE gel showing purified recombinant LC3. FIG. 3B—Diagram of the SUPR peptide mRNA display library used in this selection. FIG. 3C—Reduction in number of PCR cycles required to recover the enriched library after each round of selection indicates that higher affinity peptides for the target protein are beginning to dominate the library. FIG. 3D—Sequencing of the round seven library reveals two families of peptide sequences which dominate the final pool (Clone 4B is SEQ ID NO: 1, Clone 25C is SEQ ID NO: 2, Clone 4E is SEQ ID NO: 3, Clone 25A is SEQ ID NO: 4, Clone 25F is SEQ ID NO: 5, Clone 251 is SEQ ID NO: 6, Clone 25E is SEQ ID NO: 7, Clone 4C is SEQ ID NO: 8). Interestingly, both families resemble naturally occurring LIMs, albeit with one additional amino acid inserted between the W-site and L-site binding amino acids. Without being bound by theory, this could indicate that the conformation of the cyclic peptides differs from the mostly linear beta sheets of naturally occurring LIMs, necessitating an additional spacer amino acid. FIG. 3E—Binding analysis confirms selective LC3 binding of clones 25A (SEQ ID NO: 4), 25C (SEQ ID NO: 2), 25F (SEQ ID NO: 5), 4B (SEQ ID NO: 1), and 4E (SEQ ID NO: 3). Peptide 4B (SEQ ID NO: 1) shows nearly quantitative binding to immobilized LC3. The left column of each pair represents LC3A.

FIGS. 5A-B: Clone 4B (SUPR4B) binds to LC3. FIG. 5A—Structure of SUPR4B. N-methyl alanine residue at position 9 is shown. FIG. 5B—Surface plasmon resonance analysis indicates that SUPR4B binds to LC3 with an apparent dissociation constant of 291 μM.

FIGS. 6A&B—MTT viability assays with 50 M linear and cyclic SUPR 4B on non-DIRAS3 induced OVCAR8 (FIG. 6B) and SKOv3 (FIG. 6A) cells. Dotted line shows each cell line without Dox treatment at 72 hours. FIGS. 6C&D—

Figure 6A:
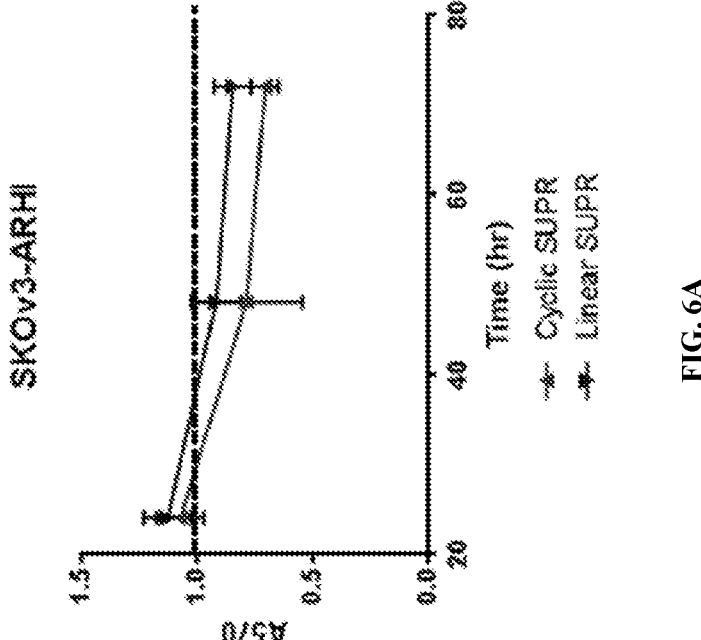
FIGS. 6A-D: SUPR4B in the DIRAS3 autophagy model.
Figure 6B:
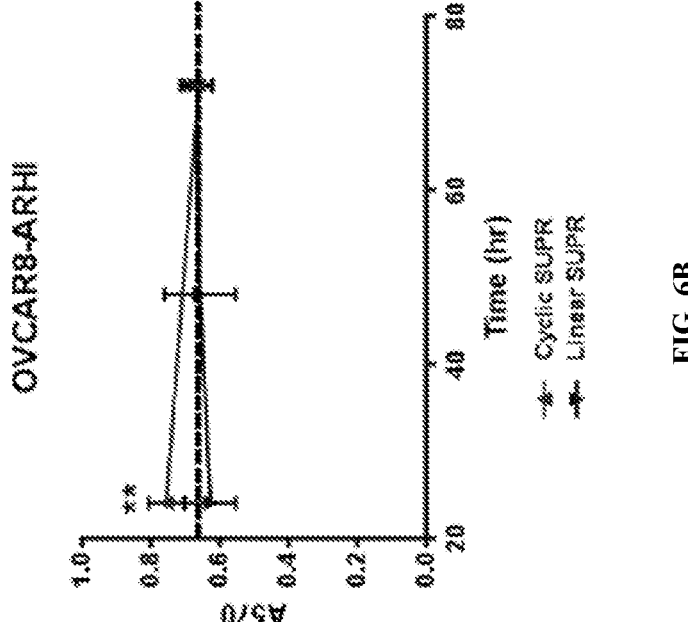
Figure 6C:
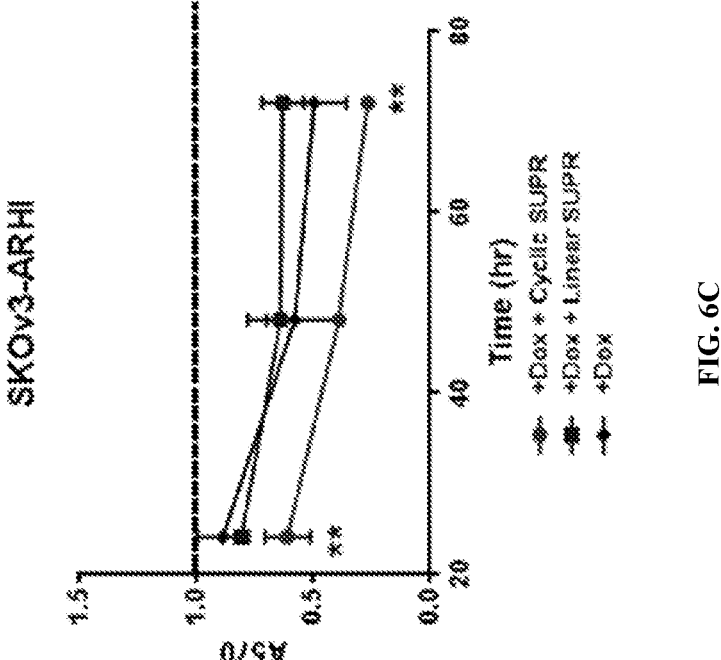
Figure 6D:
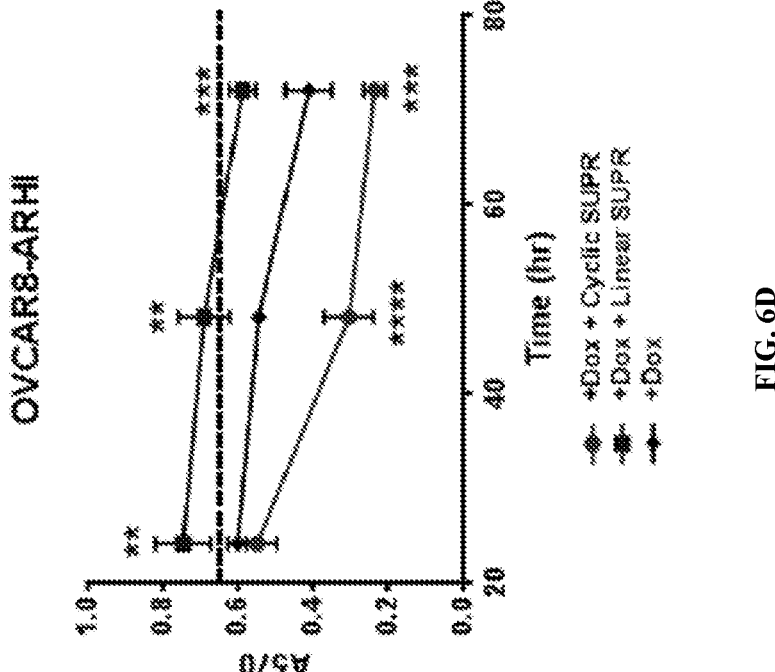

MTT viability assays on the effect of 50 M linear and cyclic LC3 SUPR 4B1W on DIRAS3-induced OVCAR8 (FIG. 6D) and SKOv3 (FIG. 6C) cells. Induction was performed using 1 g/mL DOX. Dotted line shows each cell line without Dox treatment at 72 hours.

Figure 7A:
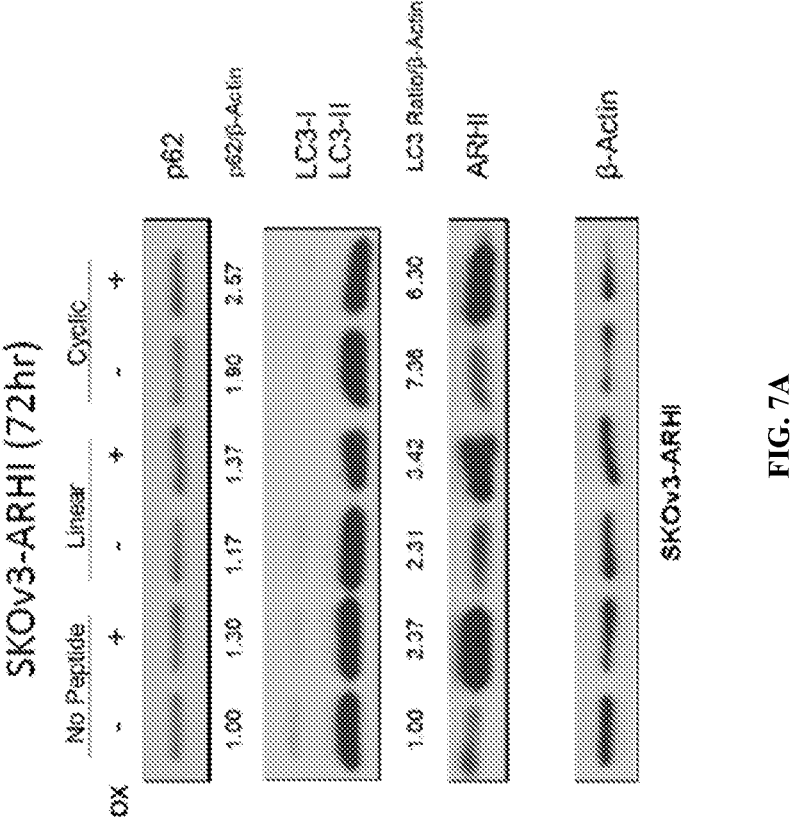
Figure 7B:
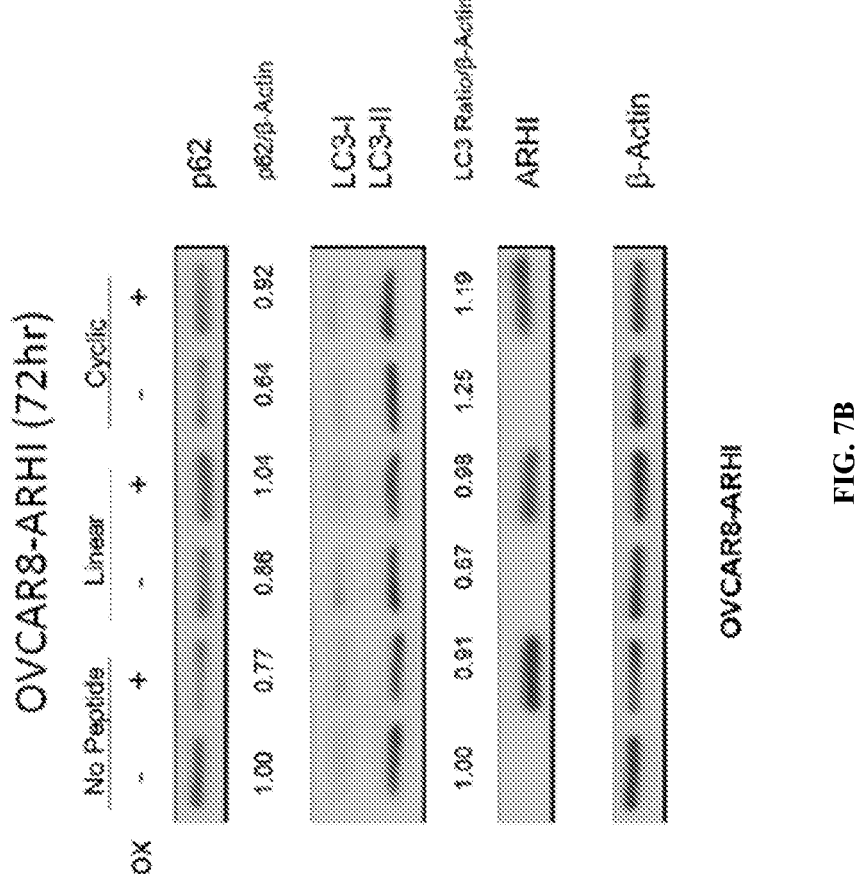

FIGS. 7A-B: SUPR4B in the DIRAS3 autophagy model. FIG. 7A—Western blotting of SKOv3-ARHI cells shows levels of p62 in autophagic, SUPR4B-treated cells along with the LC3I/LC3II ratio. FIG. 7B—Western blotting of OVCAR8-ARHI cells shows levels of p62 in autophagic, SUPR4B1W-treated cells along with the LC3I/LC3II ratio.

FIGS. 8A-F: SUPR4B in the DIRAS3 autophagy model. When autophagy is induced through forced expression of the gene DIRAS3 in this model, viability is significantly reduced within 72 hours. Inhibition of autophagy by the present compound were hypothesized to restore cellular growth. As expected, SUPR4B showed no significant toxicity in non-autophagic cells (FIGS. 8A&B) and significant restoration of viability in autophagy-induced cells (FIGS. 8C&D). FIGS. 8A&B—MTT viability assays with 50 M linear and cyclic SUPR on non-DIRAS3 induced OVCAR8 (FIG. 8A) and SKOv3 (FIG. 8B) cells. Dotted line shows each cell line without Dox treatment at 72 hours. FIGS. 8C&D—MTT viability assays on the effect of 50 M linear and cyclic LC3 SUPR4B on DIRAS3-induced OVCAR8 (FIG. 8C) and SKOv3 (FIG. 8D) cells. Induction was performed using 1 g/mL DOX. Dotted line shows each cell line without Dox treatment at 72 hours. FIGS. 8E&F—Western blots of DIRAS3-induced, peptide-treated OVCAR8 (FIG. 8E) and SKOv3 (FIG. 8F) cells after 72 h show increased intracellular p62 levels and altered LC3-1/LC3-2 ratios, again consistent with autophagy inhibition by SUPR4B.

Figure 9A:
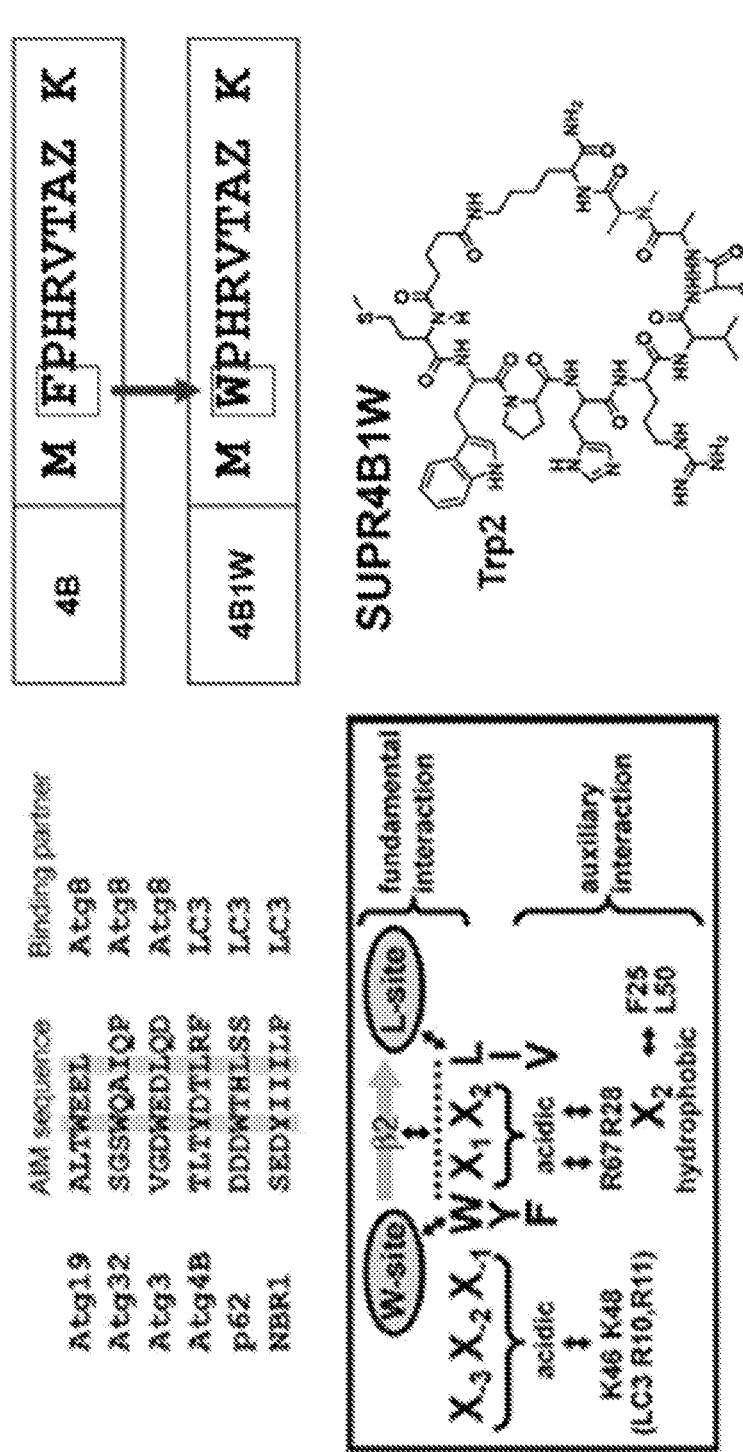
Figure 9B:
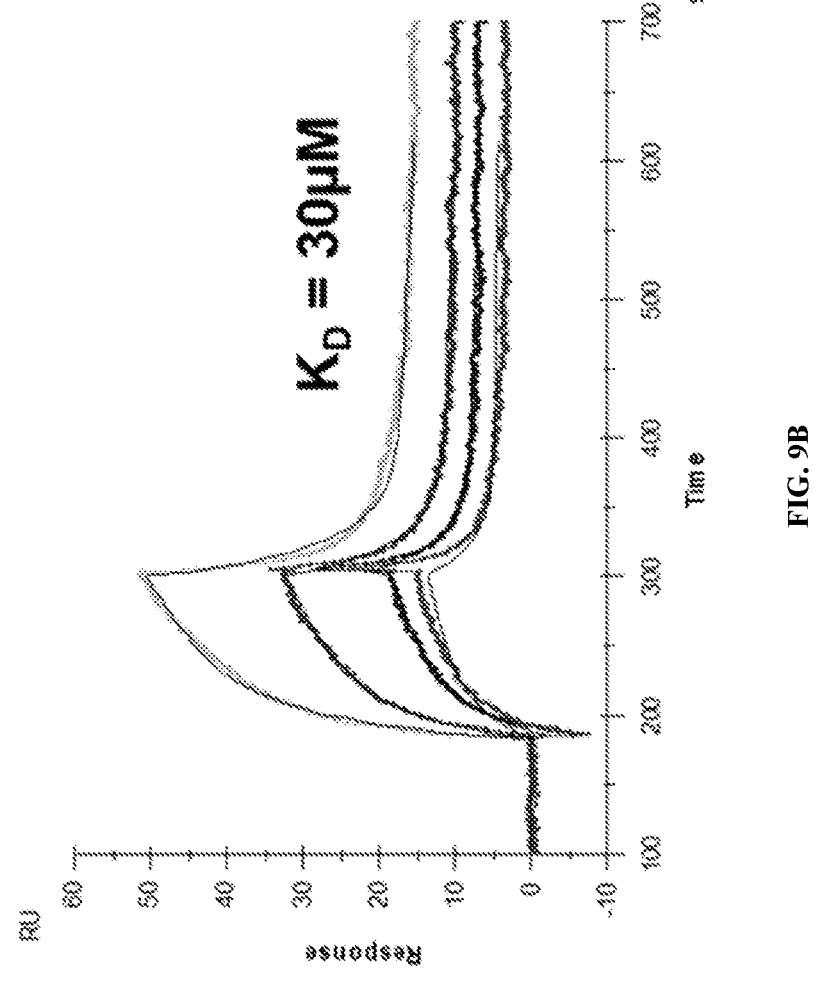
Figure 9C:
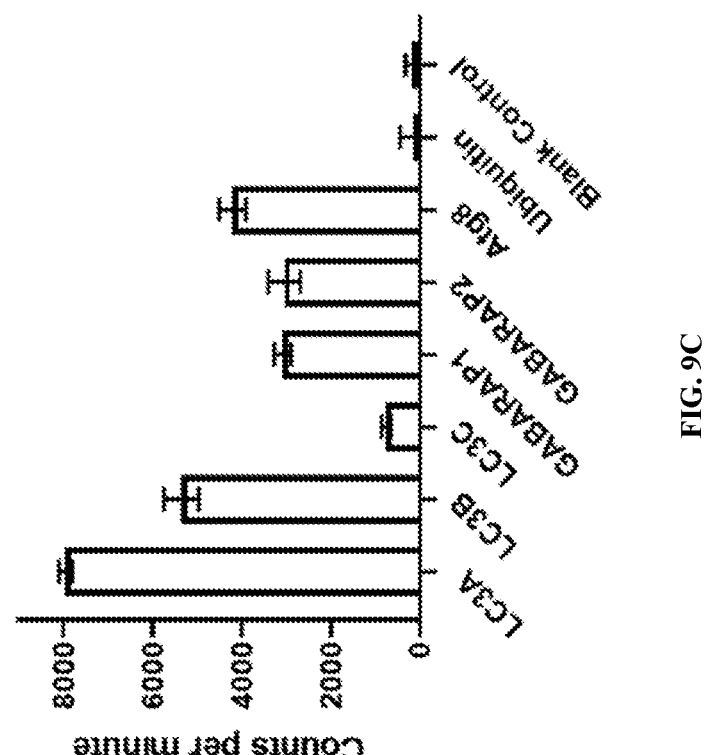
Figure 9D:
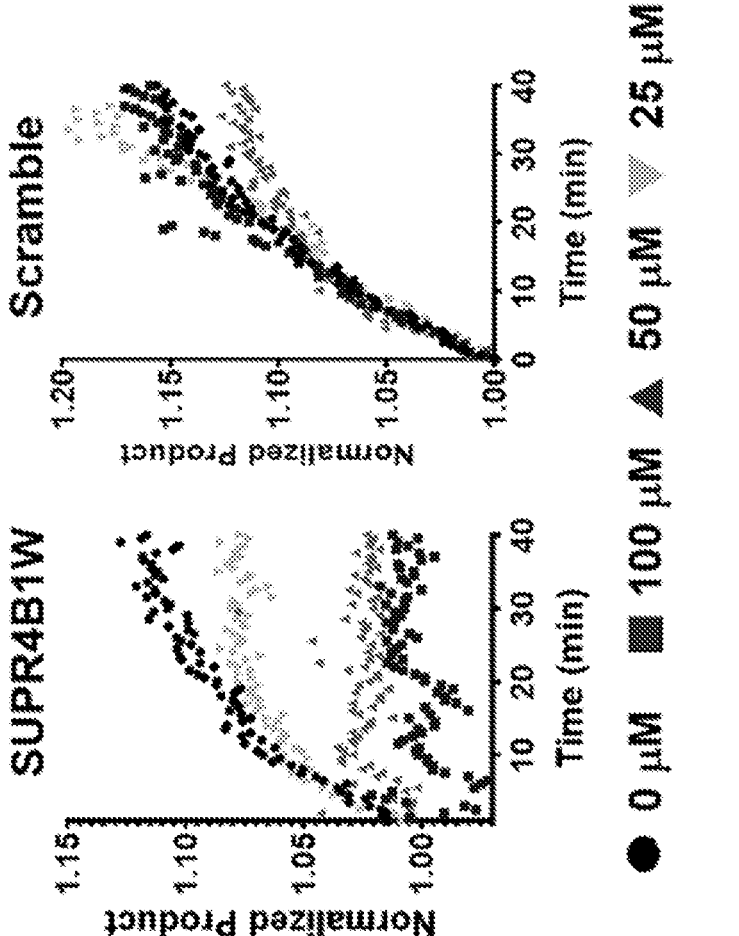

FIGS. 9A-D: Design of SUPR 4B1W. FIG. 9A—In naturally occurring LIMs, the most common amino acid in the leading position of the motif is tryptophan. Preliminary sequencing of the round 7 pool showed no peptides containing tryptophan. The reason for this may be that there exists only one codon for tryptophan, making it much less likely to appear in a selected peptide than another W-site recognizing amino acid. Modifying the lead position of SUPR 4B (SEQ ID NO: 1) from phenylalanine to tryptophan was hypothesized to produce a peptide that obtains improved binding affinity towards LC3 by more closely mimicking a naturally occurring LIM. Tryptophan may also confer increased hydrophobicity, which may enhance cell uptake. The sequence of SUPR 4B1W is provided in SEQ ID NO: 9. Atg19 is provided in SEQ ID NO: 10, Atg32 is provided in SEQ ID NO: 11, Atg3 is provided in SEQ ID NO: 12, Atg4B is provided in SEQ ID NO: 13, p62 is provided in SEQ ID NO: 14, NBR1 is provided in SEQ ID NO: 15. FIG. 9B—SPR analysis indicates that SUPR4B1W binds to LC3 with an apparent dissociation constant of 30 M. FIG. 9C—SUPR4B1W was immobilized on solid phase followed by incubation with a series of in vitro translated $S^{35}$-labeled LC3 homologs. FIG. 9D—LC3-AMC (120 nM) was incubated with Atg4B (220 pM) in the presence of SUPR4B1W or a non-functional scrambled variant at the concentrations shown. Cleavage of LC3-AMC was measured by increased fluorescence ($\lambda_{Ex}$=380 nm, $\lambda_{Ex}$=460 nm).

Figure 10A:
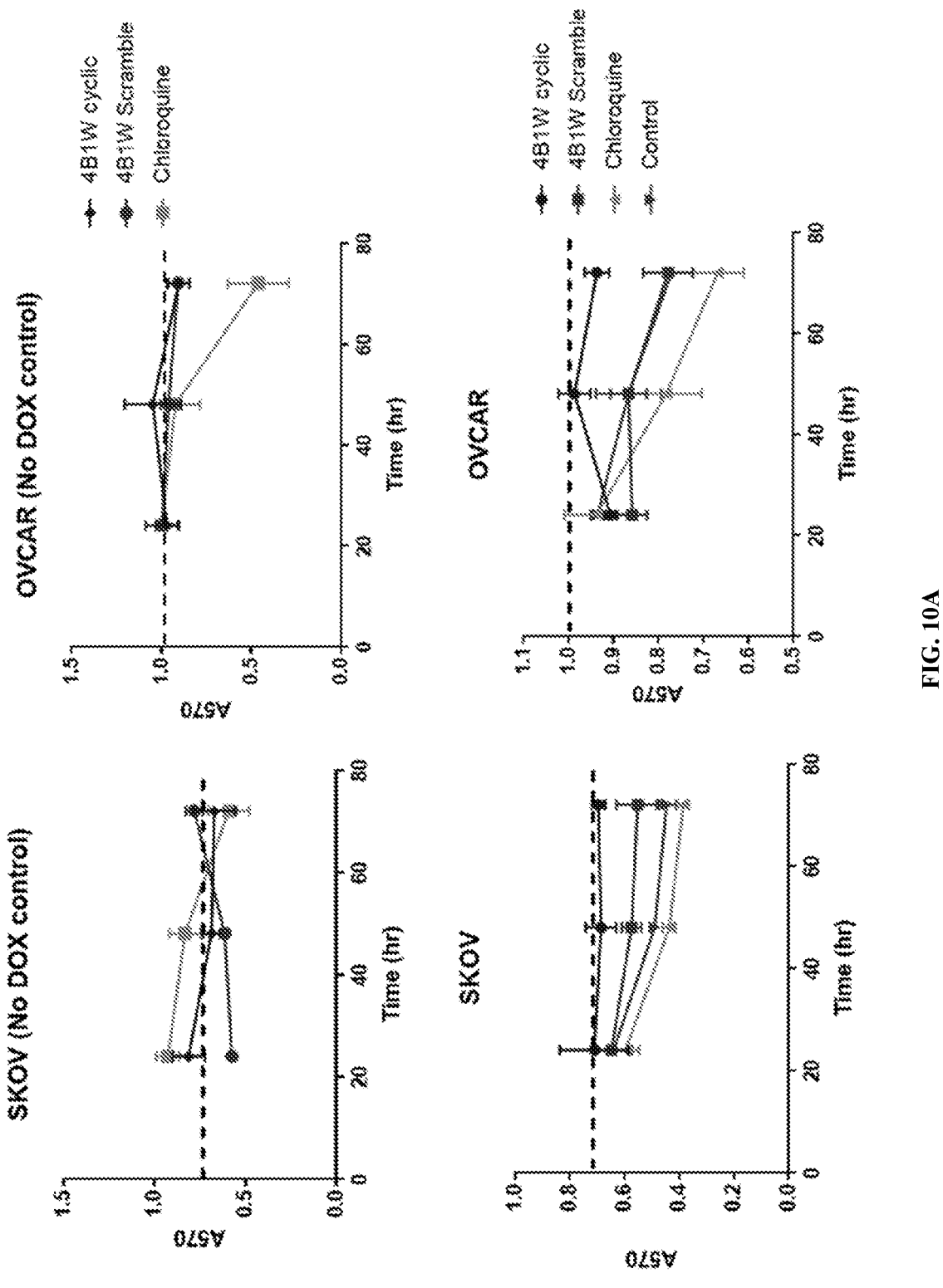

FIGS. 10A-C: SUPR4B1W inhibits autophagy in the DIRAS3 cell culture model. FIG. 10A—Treatment of non-induced SKOv3 and OVCAR8 cells with 50 M SUPR4B1W shows no change in cell viability by MTT assay over a 72 hour period (top panels). In contrast, chloroquine (CQ) shows significant toxicity in OVCAR8 cells after 72 hr. Treatment with doxycycline to induce DIRAS3 expression (bottom panels) results in a significant reduction in cell viability over 72 hours. Treatment with 50 M SUPR4B1W almost completely restores cell viability consistent with inhibition of autophagy. Treatment with a non-functional scrambled peptide or chloroquine did not result in a statistically significant increase in cell viability. FIG. 10B—Western blotting of SKOV-ARHI cells shows accumulation of p62 in autophagic, SUPR4B1W-treated cells along with a decreased LC3I/LC3II ratio. This indicates that cyclic SUPR 4B1W inhibits the LC3-mediated localization of p62 to the autophagosome where it would normally be degraded. Treatment with a linear version of SUPR4B1W did not significantly alter intracellular p62 levels. FIG. 10C—Western blotting of OVCAR8-ARHI cells shows levels of p62 in autophagic, SUPR4B1W-treated cells along with the LC3I/LC3II ratio.

FIG. 11: Confocal microscopy of SUPR 4B1W-Rox in autophagic HeLa cells. A line of HeLa cells was stably transfected with a GFP-LC3 fusion. When starved for 2+ hours in Hank's Balanced Salt Solution, these cells become autophagic and GFP signal becomes punctate as GFP-LC3 fusions are embedded in the autophagosome. SUPR 4B1W was conjugated to the fluorophore ROX and incubated with starved (autophagic) HeLa cells and observed via fluorescence confocal microscopy. Significant co-localization of ROX and GFP signal were observed, suggesting that SUPR 4B1W-ROX is binding to LC3 in the vicinity of the autophagosome.

Figure 12:
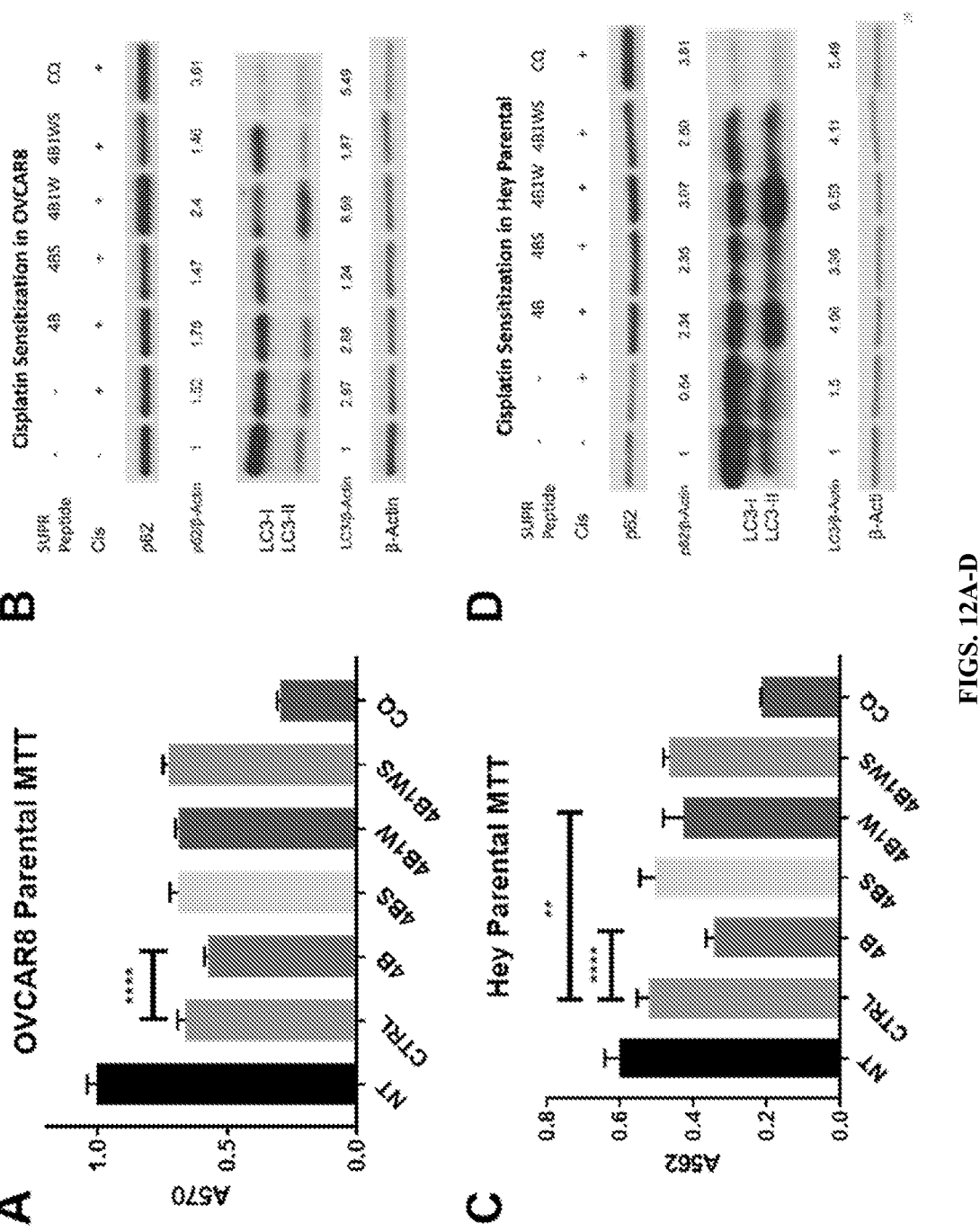

FIGS. 12A-D: SUPR4B1W sensitizes ovarian cancer cells to cisplatin. Cisplatin-resistant ovarian cancer cell lines were treated with cisplatin (10 M), combinations of cisplatin and SUPR peptide (50 M), or chloroquine (10 M) for 48 hr. FIGS. 12A&C—MTT viability assays show that combinations of SUPR peptides with cisplatin re-sensitizes resistant cell lines to cisplatin, while scrambled versions of SUPR peptides have no effect. FIGS. 12B&D—Western blots show that cisplatin/SUPR peptide combinations dramatically perturb LC3-I/LC3-II ratios and trigger accumulation of p62, suggesting inhibition of cisplatin-mediated autophagy.

Figure 13:
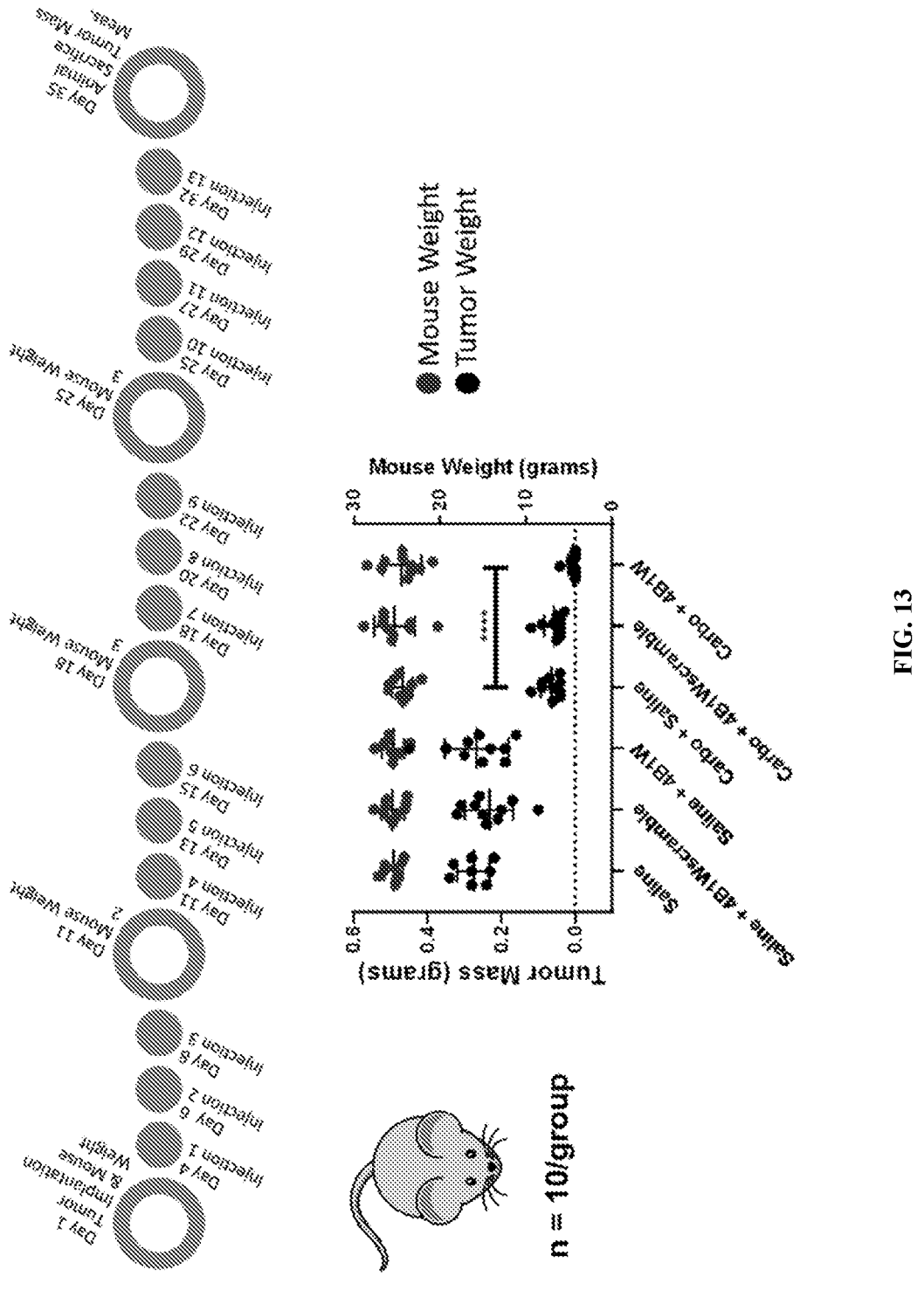

FIG. 13: SUPR4B1W sensitizes orthotopic ovarian tumors to carboplatin treatment. Mice were injected IP with 2 million OVCAR8 cells and treated three times per week for four weeks with vehicle control, SUPR peptide (10 mg/kg), carboplatin (25 mg/kg), or combination of SUPR peptide and carboplatin. At the end of four weeks, mice were sacrificed and tumors were dissected. Neither SUPR4B1W nor its scrambled version had any effect on the final tumor mass when administered alone. When combined with carboplatin, SUPR4B1W significantly reduced tumor mass and in 6 mice no tumors were detectable. The combination of carboplatin and scrambled peptides showed no changes relative to carboplatin alone. For each vertical groups of data points, the top group represents Mouse Weight and the bottom group represents Tumor Weight.

DETAILED DESCRIPTION

Autophagy is a bulk catabolic process by which misfolded proteins and damaged organelles are sequestered in intracellular vesicles called autophagosomes. Cells that undergo autophagy form double-membrane vesicles called autophagosomes that engulf proteins and organelles in the cytosol and deliver them to lysosomes for degradation. Following fusion with lysosomes, the contents of the autophagosomes are degraded into monomers, which can be used to support cellular metabolism. Autophagy plays a critical role in maintaining tumor viability during times of metabolic stress and has been shown to support both tumor dormancy and therapeutic resistance.

Two autophagy inhibitors, chloroquine and hydroxychloroquine, have been evaluated in clinical trials in which they have shown poor efficacy and unfavorable pharmacokinetics. In some studies, efficacy has only been observed at, or near, the dose-limiting toxicity, indicating a narrow therapeutic window. The toxicity of these compounds may be related to their mechanism of action—both accumulate in lysosomes and raise the pH, effectively shutting down lysosomal hydrolases and inhibiting degradation of lysosomal contents. While this results in blockade of autophagic flux, it also interferes with normal lysosomal processes, which may contribute to non-selective toxicity.

Although autophagy plays a crucial role in tumor suppression and evasion of chemotherapy, there are no targeted inhibitors of autophagy and imaging is limited to transfection techniques in cell culture. Human microtubule-associated protein light chain 3 (MAP1LC3 or LC3) is a small ubiquitin-like protein that plays a critical role in the formation of autophagosomes and recruitment of cytosolic proteins and organelles to the autophagosome interior. Due to playing an essential role in the progression of autophagy, LC3 represents a promising target for inhibition and imaging of autophagy.

LC3-interacting motifs have been previously identified through sequence analysis of proteins that bind to LC3. These motifs are characterized by the peptide sequence W/Y/F-X-X-L/I/V, where X can be any amino acid. While these have been shown to bind to LC3 and block LC3-mediated protein-protein interactions in vitro, they have never been shown to inhibit LC3 function and autophagy in living cells. This is likely due to (1) the relatively low affinity of these short, linear peptides for the LC3 functional binding site, (2) their low stability to cellular proteases and hydrolases, and (3) their poor cellular permeability.

Provided herein are macrocyclic peptides that bind tightly to LC3. These peptides contain a non-canonical LC3-interacting motif (F/Y/W-X-X-X-I/L/V) along with a conserved N-methylalanine at position 9 within the macrocycle. Binding to LC3 disrupts key protein-protein interactions (e.g., with atg4b and p62) that are required for autophagosome formation and function. These peptides readily cross the cell membrane at micromolar concentrations and disrupt autophagy in a cell-based model of ovarian cancer dormancy. In contrast to chloroquine, an autophagy inhibitor currently in clinical trials, the present LC3-binding peptides are highly selective and show no apparent toxicity at mid-micromolar concentrations. The cyclic peptides disclosed herein can be used to (1) inhibit the survival of dormant tumors during chemotherapy; (2) inhibit the survival of tumors during radiotherapy; and (3) visualize autophagosome formation and localization in living cells.

I. CYCLIC PEPTIDES

In certain embodiments, the present invention concerns novel compositions comprising at least one peptide, such as a cyclic peptide autophagy inhibitor that binds to LC3.

As used herein, a protein generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide" and "peptide may be used interchangeably herein.

In certain embodiments the size of the at least one peptide may comprise, but is not limited to, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown in Table 1.

TABLE 1

| Modified and Unusual Amino Acids | | | |
|---|---|---|---|
| Abbr. | Amino Acid | Abbr. | Amino Acid |
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | Z | N-Methylalanine |
| Baib | 3-Aminoisobutyric acid | MeGly | N-Methylglycine, sarcosine |
| Apm | 2-Aminopimelic acid | MeIle | N-Methylisoleucine |
| Dbu | 2,4-Diaminobutyric acid | MeLys | 6-N-Methyllysine |
| Des | Desmosine | MeVal | N-Methylvaline |
| Dpm | 2,2'-Diaminopimelic acid | Nva | Norvaline |
| Dpr | 2,3-Diaminopropionic acid | Nle | Norleucine |
| EtGly | N-Ethylglycine | Orn | Ornithine |

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). Alternatively, various commercial preparations of proteins, polypeptides and peptides are known to those of skill in the art.

Substitution or replacement variants typically contain the exchange of one amino acid for another at one or more sites within the protein or peptide and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein or peptide may possess an insertion of residues, which typically involves the addition of at least one residue in the protein or peptide. This may include the insertion of a targeting peptide or polypeptide or simply a single residue.

A. Peptide Synthesis

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid residue having its carboxyl group and other reactive groups protected and the free primary carboxyl group of another amino acid residue having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the cyclic peptides of the present invention.

The process for synthesizing the cyclic peptides may be carried out by a procedure whereby each amino acid residue in the desired sequence is added one at a time in succession to another amino acid residue or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods.

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods. Alpha amino groups may be protected by a suitable protecting group, including a urethane-type protecting group, such as benzyloxycarbonyl and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc is preferred for alpha amino protection. Guanidino groups may be protected by a suitable protecting group, such as nitro, p-toluenesulfonyl (Tos), benzyloxycarbonyl, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin, a 2-chlorotrityl chloride resin or an oxime resin, by an amide bond between an Fmoc-Linker, such as p-[(R,S)-α-[1-(9H-fluor-en-9-yl)-methoxyformamido]-2,4-dimethyloxyben-zyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide. Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, used for other amino acids with amino group-containing side chains. Thus, for example, Fmoc-Lys (Pbf)-OH and Fmoc-Glu(OAII)-OH amino acids (Glu (OAII) refers to glutamic acid 5-allyl ester) can be employed for the positions forming a lactam bridge upon cyclization, while other amino acids with amino group-containing side chains have a different and orthogonal protecting group, such as with Fmoc-Arg(Pbf)-OH, Fmoc-Orn(Alloc)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminal modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

1. Cyclization

The peptides disclosed herein are cyclized. Any method of cyclization may be employed. For example, cyclization may be carried out by crosslinking the N-terminal amino group with the side chain of the invariant lysine at position 10 using the di-succinimidyl glutarate crosslinker.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzo-triazol-1-yl)-1,1,3,3-tetramethyluronium hexafluorophosphate (HBTU), benzotriazole-1-yl-oxy-tris(dimethylamino) phosphoniumhexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/i-hydroxybenzo-triazole (DCCI/HOBt). Coupling is conventionally initiated by use of a suitable base, such as N,N-diisopropylethylamine (DIPEA), sym-collidine or N-methylmorpholine (NMM).

The cyclized peptides can then be cleaved from solid phase, using any suitable reagent, such as ethylamine in DCM or various combinations of agents, such as trifluoroacetic acid (TFA), tri-isopropylsilane (TIS), dimethoxy-benzene (DMB), water and the like. The resulting crude peptide is dried and remaining amino acid side chain protecting groups, if any, are cleaved using any suitable reagent, such as TFA in the presence of water, TIS, 2-mercaptopethane (ME), and/or 1,2-ethanedithiol (EDT). The final product may be precipitated by adding cold ether and collected by filtration. Final purification is by reverse phase high performance liquid chromatography (RP-HPLC), using a suitable column, such as a C18 column, or other methods of separation or purification, such as methods based on the size or charge of the peptide, may also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn et al. (1996); DeGrado and Kaiser (1982). Such a starting material can be prepared by attaching an alpha amino-protected amino acid by an ester linkage to a p-benzyloxybenzyl alcohol (Wang) resin, by amide linkage to a 4-(2',4'-dime-thoxylphenyl-aminomethyl-phenoxy (Rink Amide) resin, or an oxime resin, by well known means. The peptide chain is grown with the desired sequence of amino acids. Before cleavage, the peptide is cyclized on the solid phase, and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, peptides employing a Rink Amide resin may be cleaved by mixture of TFA, TIS and water, and peptides employing an oxime resin may be cleaved by DCM. While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

2. Lipidation

Peptides need not be lipidated, but it may be advantageous for certain peptides to be lipidated with any acceptable lipid, such as palmitic acid (C16) or stearic acid (C18), so as to allow a peptide to pass through a lipid bilayer. Peptides incorporating lipidation may benefit from placement of a KSS motif at their N-termini. The peptides incorporating lipidation may contain one or more lipid moieties, for example, two lipid moieties per peptide. Lipidated peptides may move more easily through the cytoplasm and lipid bilayer.

For lipidation, a lipid chain can be a C12 to C20 lipid chain. C16 and C18 lipid chains are preferred. The cyclic peptides can be lipidated by any conventional or acceptable method known in the art to introduce lipids to peptides. This can be achieved by attaching one or more lipid moieties to the peptides. There are several ways for introducing lipids. The lipids can be attached via an oligopeptide spacer at either the N- or C-terminus of the peptides between the peptide and the lipid moiety. The oligopeptide can comprise any number of amino acid residues and the lipid moiety can be attached to any of the amino acid residues in the oligopeptide. The lipid moiety may be bulky and may be added to the N-terminal end of the oligopeptide such that it is separated from the amino acids of the peptide to prevent any possible interference with functional portions, for example, of the amino acids in the cyclic peptides. A suitable spacer may be selected for the particular application used. Usually, a spacer comprises no more than 3 amino acids that are relatively simple in structure (such as, but not limited to, serine, glycine or asparagine, for example). Serine is suitable as it increases the solubility of lipidated peptides in water. Also, it is advantageous to include lysine in the oligopeptide, which permits the addition of two lipid moieties. Alternatively, the peptides can be lipidated directly without using a spacer at all. In this way, either the N- or C-terminal amino acid residue of the peptide is itself lipidated. Finally, the peptide can undergo total lipidation, i.e., one or more residues of the peptide can be lipidated. One advantage of total lipidation is that the peptides can be purified first, then lipidated. This overcomes some of the problems associated with the purification of lipidated peptides.

3. PEGylation

PEGylation is a method well known to those skilled in the art wherein a polypeptide compound (for the purposes of the present invention, a cyclic peptide autophagy inhibitor or the functional analogue or variant) is modified such that one or more polyethylene glycol (PEG) molecules are covalently attached to the side chain of one or more amino acids or derivatives thereof. Other molecule altering structural chemistry techniques may be used; such techniques may improve the pharmacodynamic properties of the molecule, for example extending its half-life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., 2001). Methods that may be used to covalently attach the PEG molecules to polypeptides are further described in Roberts et al. (2002), Bhadra et al. (2002), Kozlowski et al. (2001), Veronese (2001), and references referred to therein.

The advantages of PEGylation of the peptide or peptidomimetic compounds of the invention include prolonged circulatory time due to reduced renal clearance resulting from increased hydrodynamic size (size in solution) of the agent which, for some products, results in a more sustained adsorption after administration as well as restricted distribution, possibly leading to a more constant and sustained plasma concentrations and hence an increase in clinical effectiveness (Harris et al., 2001). Further advantages can include reduced immunogenicity of the therapeutic compound (Reddy, 2001), and lower toxicity (Kozlowski et al., 2001).

The first step in PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc. made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homodimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However; this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However; this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

II. TREATMENT OF DISEASE

Certain aspects of the present embodiments can be used to prevent or treat a disease or disorder associated with autophagy. LC3 may be inhibited by any suitable drugs to prevent protein-protein interactions that are required for autophagy. Preferably, such substances would be cyclic peptide inhibitors of LC3.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a cyclic peptide that inhibits LC3.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, inhibition of dormant tumor viability, or prevention of metastasis. Treatment of cancer may also refer to prolonging survival of a subject with cancer.

A cyclic peptide that inhibits LC3 may be administered to treat a cancer. The cancer may be a solid tumor, metastatic cancer, or non-metastatic cancer. For example, the peptides may be administered to ovarian cancer patients (1) in an adjuvant setting to enhance the effect of cisplatin or (2) as a chemopreventive to inhibit the survival of autophagic, dormant nodules following initial therapy. As such, a cyclic peptide may be administered long-term to prevent recurrence. These peptides may also provide therapeutic benefit to patients with pancreatic cancer where autophagy plays a key role in tumor growth and treatment resistance. These peptides may enhance the efficacy of radiation therapy in cases where radiotherapy resistance is associated with up-regulation of autophagy.

In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

A cyclic peptide that inhibits LC3 may be administered to treat neurodegeneration, inflammation, Crohn's disease, various myopathies, liver disease, or heart disease.

A. Pharmaceutical Compositions

Where clinical application of a therapeutic composition containing an inhibitory cyclic peptide is undertaken, it will generally be beneficial to prepare a pharmaceutical or therapeutic composition appropriate for the intended application. This will typically entail preparing a pharmaceutical composition that is essentially free of pyrogens, as well as any other impurities that could be harmful to humans or animals.

One may also employ appropriate buffers to render the complex stable and allow for uptake by target cells. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising a cyclic peptide or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired.

The actual dosage amount of a composition of the present embodiments administered to a patient or subject can be determined by physical and physiological factors, such as body weight, age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 g/kg/body weight to about 1000 mg/kg/body weight (this such range includes intervening doses) or more per administration, and any range derivable therein. In non-limiting examples of a derivable range from the numbers listed herein, a range of about 5 g/kg/body weight to about 100 mg/kg/body weight, about 5 g/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, or respiratory tract, aerosol delivery can be used. Volume of the aerosol is between about 0.01 mL and 0.5 mL.

An effective amount of the therapeutic composition is determined based on the intended goal. For example, one skilled in the art can readily determine an effective amount of a cyclic inhibitory peptide of the invention to be administered to a given subject. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are particular to each individual. Factors affecting the dose include the physical and clinical state of the patient, the route of administration, the intended goal of treatment and the potency, stability and toxicity of the particular therapeutic substance.

B. Combination Treatments

In certain embodiments, the compositions and methods of the present embodiments involve a cyclic peptide LC3 inhibitor to inhibit autophagy, in combination with a second or additional therapy. Such therapy can be applied in the treatment of any disease that is associated with autophagy. For example, the disease may be cancer. The administration may include long-term, chronic administration to prevent recurrence.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both a cyclic inhibitory peptide and a second therapy. A tissue, tumor, or cell can be contacted with one or more compositions or pharmacological formulation(s) comprising one or more of the agents (i.e., cyclic peptide or an anti-cancer agent), or by contacting the tissue, tumor, and/or cell with two or more distinct compositions or formulations, wherein one composition provides 1) a cyclic peptide, 2) an anti-cancer agent, or 3) both a cyclic peptide and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory cyclic peptide may be administered before, during, after, or in various combinations relative to an anti-cancer treatment. The administrations may be in intervals ranging from concurrently to minutes to days to weeks. In embodiments where the cyclic peptide is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the cyclic peptide and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a cyclic peptide therapy is "A" and an anti-cancer therapy is "B":

A/B/A B/A/B B/B/A A/A/B A/B/B B/A/A A/B/B/B B/A/ B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. For example, the cyclic peptides provided herein may be administered in combination with another anti-autophagy drug, such as, for example, an mTOR inhibitors (e.g., rapamycin), chloroquine, and/or hydroxychloroquine.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, carboplatin, nedaplatin, and picoplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as 7-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, *Nat Rev Cancer,* 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immuno-globulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen bind-ing fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Applica-tion Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodi-ments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lympho-cyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human-ized antibody, or a chimeric antibody), an antigen binding fragment thereof, an immunoadhesin, a fusion protein, or oligopeptide. Anti-human-CTLA-4 antibodies (or VH and/ or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) Proc Natl Acad Sci USA, 95(17): 10067-10071; Camacho et al. (2004) J Clin Oncology, 22(145): Abstract No. 2505 (antibody CP-675206); and Mokyr et al. (1998) Cancer Res, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Appli-cation No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody com-prises the heavy and light chain CDRs or VRs of ipilim-umab. Accordingly, in one embodiment, the antibody com-prises the CDR1, CDR2, and CDR3 domains of the VH region of ipilimumab, and the CDR1, CDR2, and CDR3 domains of the VL region of ipilimumab. In another embodi-ment, the antibody competes for binding with and/or binds to the same epitope on CTLA-4 as the above-mentioned antibodies. In another embodiment, the antibody has an at least about 90% variable region amino acid sequence iden-tity with the above-mentioned antibodies (e.g., at least about 90%, 95%, or 99% variable region identity with ipilim-umab). Other molecules for modulating CTLA-4 include CTLA-4 ligands and receptors such as described in U.S. Pat. Nos. 5,844,905, 5,885,796 and International Patent Appli-cation Nos. WO1995001994 and WO1998042752; all incor-porated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank acces-sion number NP-002277. LAG-3 is found on the surface of activated T cells, natural killer cells, B cells, and plasma-cytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immu-noadhesin, a fusion protein, or oligopeptide. Anti-human-LAG-3 antibodies (or VH and/or VL domains derived there-from) suitable for use in the present methods can be generated using methods well known in the art. Alterna-tively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. KITS

The present invention provides kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a cyclic peptide inhibitor of LC3, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes a cyclic peptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Macrocyclic Peptides for Targeted Inhibition of Autophagy

Figures 1, 2A:
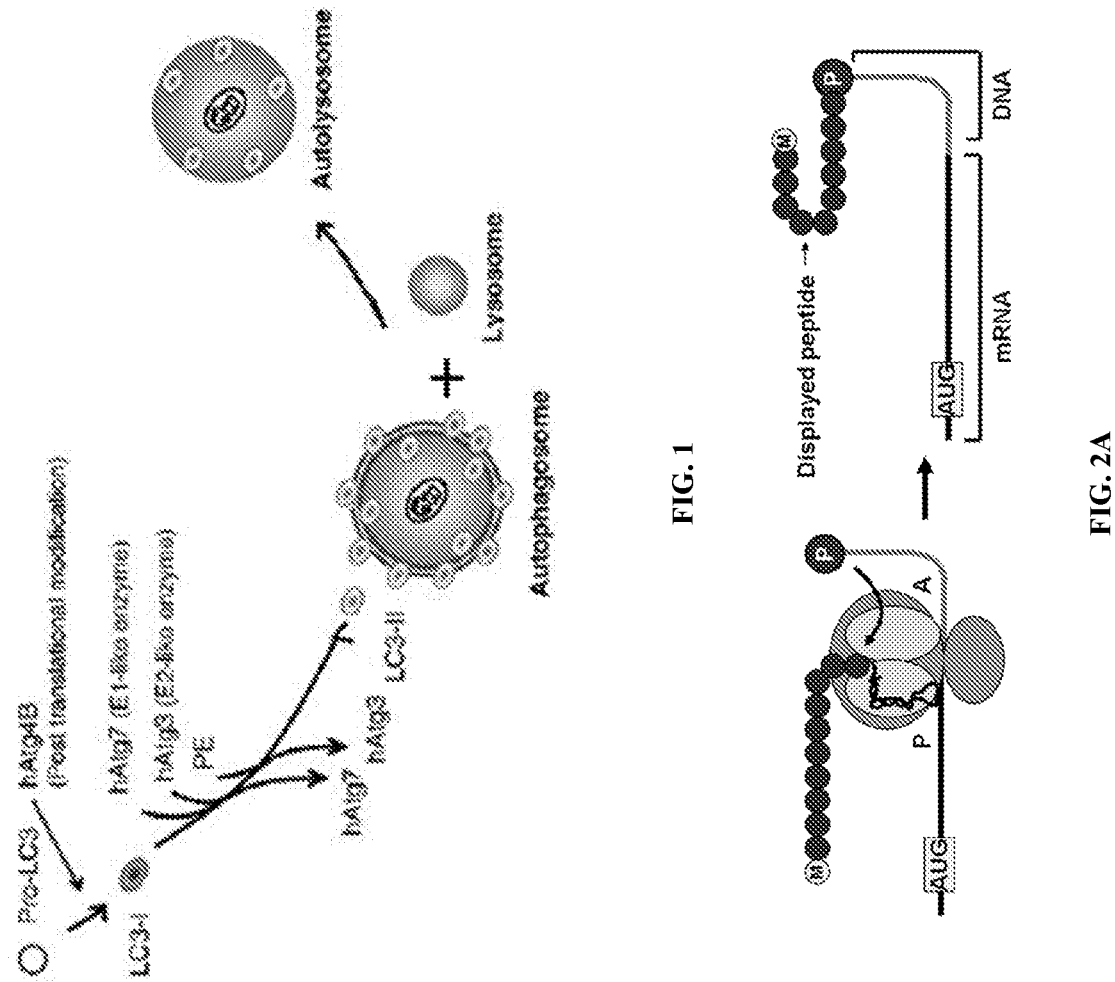
FIG. 1: Post-translational modification scheme depicting the role of LC3 in the autophagic machinery. LC3 is post-translationally cleaved at the C-terminus by the enzyme Atg4B to generate LC3-I. LC3-I is then distributed uniformly through the cytosol. Upon induction of autophagy, LC3-I is converted to LC3-II by attachment of the membrane lipid phosphatidylethanolamine to its C-terminus in a series of E1- and E2-like reactions. LC3-II is embedded in the nascent autophagosome surface where it plays an essential role in maturation of the autophagosome and transfer of cytosolic cargo to the autophagosome interior. Prior to fusion of the autophagosome and the lysosome, enzyme Atg4B recycles much of the LC3-II from the autophagosome surface back to cytosolic LC3-I by again cleaving the molecule at its C-terminus. Adapted from Kadowaki et al. (2006).
FIGS. 2A-B: Schematic of SUPR mRNA Display Selections.
Figure 2B:
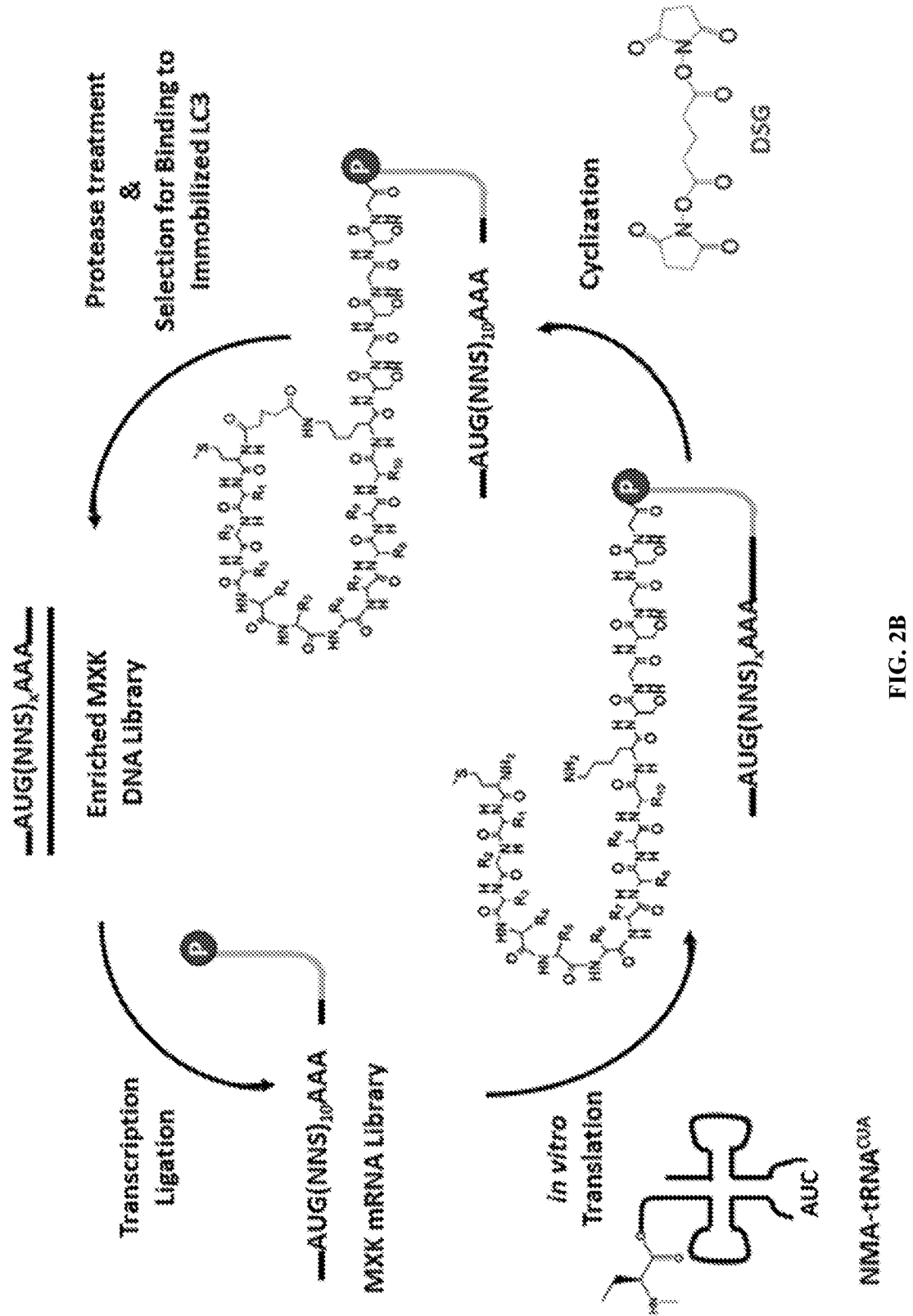

LC3, an 18 kDa ubiquitin-like protein, plays a critical role in the maturation of autophagosomes and the selective recruitment of cargo to the autophagosome interior (FIG. 1). Novel ligands that selectively bind to LC3 could be of immense value for tracking autophagy in living cells and for disrupting protein-protein interactions critical for autophagosome function. By disrupting autophagosome formation and maturation, rather than inhibiting the lysosome-which plays essential roles in many essential cellular processes in both normal and malignant tissue-much of the normal-tissue toxicity associated with CQ treatment can be avoided while still achieving a synergistic anti-tumor effect when combined with chemotherapy or radiation. SUPR (Scanning Unnatural Protease Resistant) peptide mRNA display has been used to design LC3-targeted macrocyclic peptides for inhibition and molecular imaging of autophagy. SUPR peptide mRNA display is a directed evolution process in which translated peptides are covalently bound to their encoding mRNA allowing trillions of unique peptide sequences to be iteratively sieved for binding to a target protein (FIGS. 2A-B). SUPR peptide mRNA display libraries incorporate macrocyclization and N-methyl amino acids through amber codon nonsense suppression to achieve excellent protease resistance and conformational stability. By incorporating unnatural, N-methyl amino acids and post-translational cyclization, and by screening against powerful proteases, it is possible to generate peptides with extraordinary metabolic stability and nanomolar binding affinities. These SUPR peptides bind target proteins with antibody-like affinities while potentially maintaining the tumor- and cell-penetrating properties of small molecules.

Figure 4:
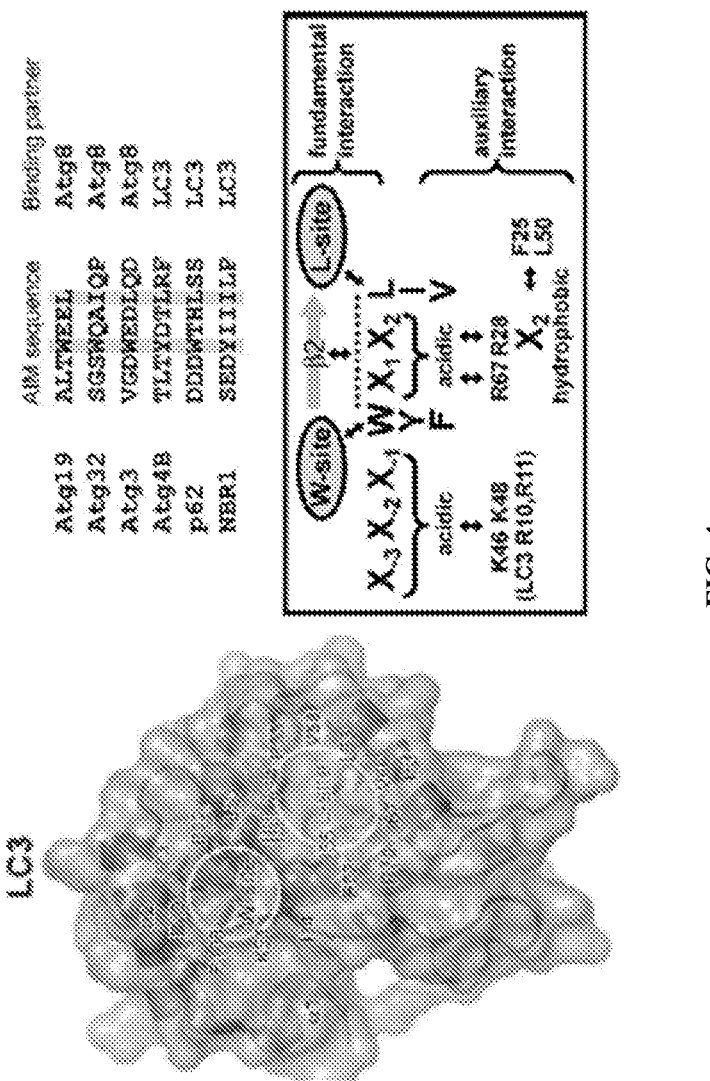
FIG. 4: Functional binding surface of LC3 and its yeast homologue Atg8. LC3 contains two hydrophobic binding pockets that recognize a (WYF)-XX-(LIV) amino acid motif called the LC3-Interacting Motif (LIM) found in most autophagy-related proteins that bind LC3. A directed evolution SUPR peptide mRNA display selection was used to produce peptides that mimic the LIM while obtaining far superior serum stability and cell-penetrating properties than natural linear LIMs while also improving binding affinity to the point where disrupting the protein-protein interactions between LC3 and the autophagic machinery becomes feasible. Exemplary LIMs from known LC3-binding proteins are shown. Adapted from Noda et al. (2010). Atg19 is provided in SEQ ID NO: 10, Atg32 is provided in SEQ ID NO: 11, Atg3 is provided in SEQ ID NO: 12, Atg4B is provided in SEQ ID NO: 13, p62 is provided in SEQ ID NO: 14, NBR1 is provided in SEQ ID NO: 15.

A randomized 8-mer peptide library (with a diversity of $3.78 \times 10^{10}$ unique sequences) was designed, and SUPR peptide mRNA display selections incorporating N-methyl alanine and proteinase-K screening were performed against recombinant LC3 (FIGS. 3A-E). For this, milligram quantities of His6-LC3A were bacterially expressed and purified, chemically biotinylated, and immobilized on streptavidin agarose resin for binding selection. Prior to each round of selection, mRNA-fusion libraries were translated using an in vitro rabbit reticulocyte lysate system incorporating amber-codon nonsense suppression with N-methyl alanine. Fusions were cyclized between the side chain of lysine and the N-terminus and briefly exposed to proteinase K to eliminate any sequences particularly susceptible to proteolysis. Binding selections were carried out by incubating mRNA display libraries with the immobilized His6-LC3A followed by elution in SDS and PCR amplification. After seven rounds of binding selection, the number of PCR cycles required to recover the enriched dsDNA after each binding selection had reduced by 40% (FIG. 3C). Sequencing showed that the library had converged significantly and was dominated by three main families of sequences. Over 90% of sequences in the library contained an N-methyl alanine residue at a conserved position adjacent to the fixed lysine residue. The highly conserved inclusion and position suggests that this unnatural residue plays a key role in enforcing cyclic peptide conformation and function (FIG. 3D). The majority of sequences contained variations of the canonical Autophagy-Interacting Motif observed in natural LC3 adaptor proteins (FIG. 4). Interestingly, these peptides show an additional residue between the W/F/Y and L/IV binding residues. Binding was confirmed by incubation of radiolabeled individual peptide fusions with immobilized LC3A (FIG. 3E; Table 2).

TABLE 2

| | LC3-Binding SUPR Peptides | |
|---|---|---|
| Clone | Sequence (SEQ ID NO:) | % of radiolabeled peptide-fusions bound to immobilized LC3 |
| 4B | MFPHRVTAZK (SEQ ID NO: 1) | 86 |
| 25C | MFSHRVTLZK (SEQ ID NO: 2) | 13 |
| 4E | MLSDIPVNDK (SEQ ID NO: 3) | 7 |
| 25A | MYARSLRDZK (SEQ ID NO: 4) | 6 |
| 25F | MNARSLRDZK (SEQ ID NO: 5) | 5 |
| 25I | MLARSLRDZK (SEQ ID NO: 6) | 4 |
| 25E | MYTRRVRLZK (SEQ ID NO: 7) | 3 |
| 4C | MSLHRVTVZK (SEQ ID NO: 8) | 1 |

Figure 5A:
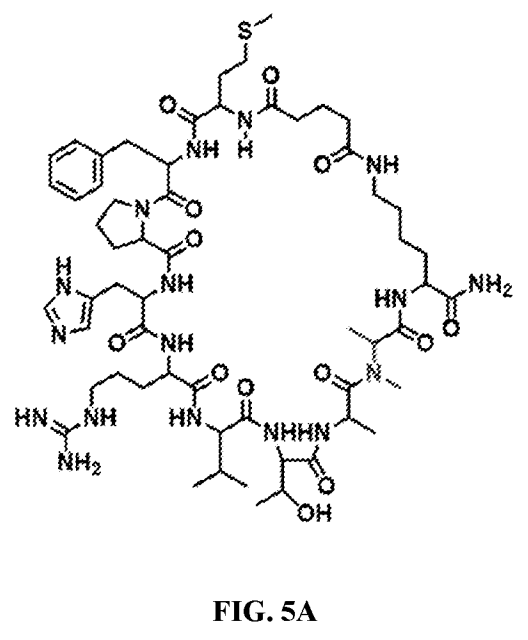
Figure 5B:
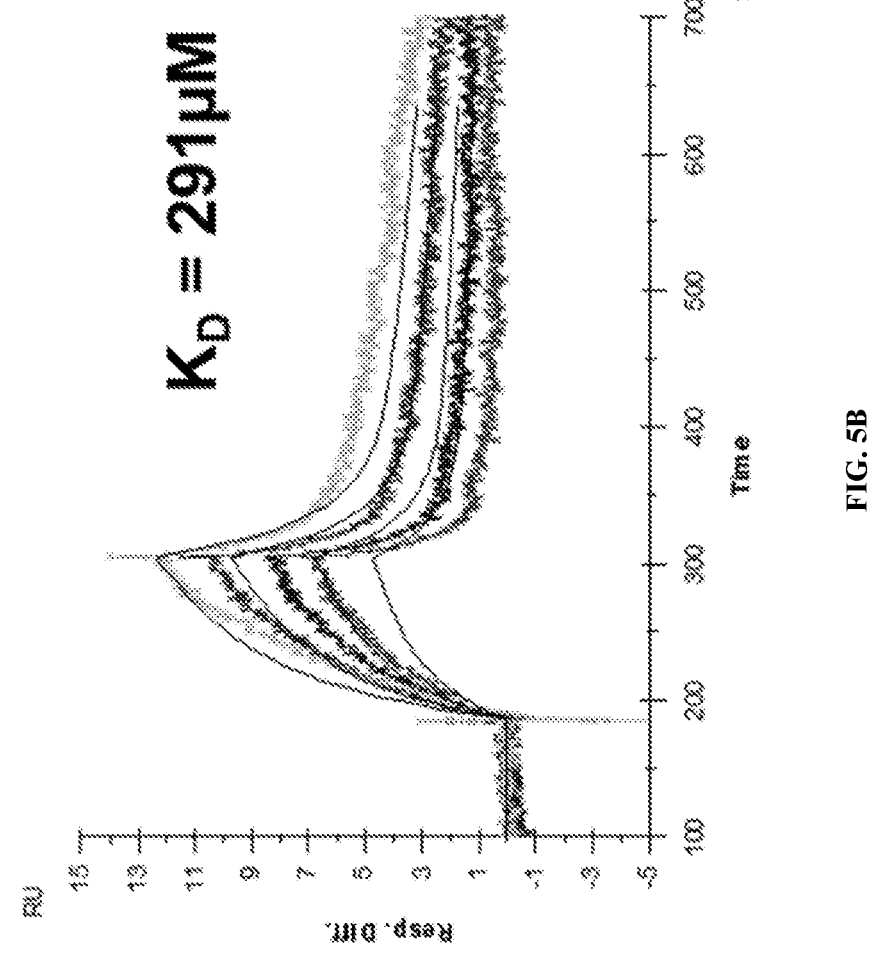

After selection, the library was sequenced and lead compounds were subjected to thermodynamic and cellular assays to develop a structure-activity relationship modeling the interaction between the SUPR peptide and the target. Binding analysis of individual clones confirmed the presence of LC3-binding sequences and indicated several residues within and surrounding the modified LIM that play a significant role in peptide affinity. The most promising candidate, SUPR 4B (FIG. 5A), was synthesized and tested for binding to LC3 using surface plasmon resonance, which indicated an apparent dissociation constant of 291 M (FIG. 5B). In addition, SUPR 4B was tested in two ovarian cancer cell lines where expression of the DIRAS3 protein is selectively induced by doxycycline (Dox) treatment (FIGS. 6A-D & 7A-B & 8A-F). In this model, DIRAS3 expression rapidly induces autophagy which significantly reduces cell viability within 48 hours. Treatment of both cell lines with 50 M SUPR 4B in the absence of DIRAS3 induction showed no statistically significant effect on cell viability, indicating absence of toxicity in non-autophagic cells. In contrast, addition of SUPR 4B to Dox-treated (autophagic) cells results in significant rescue of viability indicating autophagy inhibition. Biochemical analysis of SUPR 4B-treated cells showed an increase in p62 protein levels and a decreased LC3I/LC3II ratio supporting autophagy inhibition through blockade of LC3-mediated protein-protein interactions.

Based on other known LIM sequences, a phenylalanine-to-tryptophan substitution was made at position 2 to generate the SUPR 4B1W variant (FIG. 9A; SEQ ID NO: 9). SUPR 4B1W was tested for binding to LC3 using surface plasmon resonance, which indicated an apparent dissociation constant of 30 M, nearly a 10-fold improvement relative to SUPR4B (FIG. 9B). In addition, SUPR 4B1W was tested for binding to various LC3 homologs and orthologs. SUPR 4B1W bound tightly to LC3A and LC3B with moderate off-target binding to GABARAP1, GABARAP2, and the yeast LC3 ortholog, Atg8 (FIG. 9C). Almost no binding to LC3C or ubiquitin was observed. In order to determine whether SUPR 4B1W could inhibit the Atg4B:LC3-AMC interaction, LC3-AMC (120 nM) was incubated with Atg4B (220 pM) in the presence of SUPR4B1W or a non-functional scrambled variant at various concentrations. Cleavage of LC3-AMC was measured by increased fluorescence. The addition of increasing concentrations of SUPR4B1W resulted in significantly decreased fluorescent signal indicating inhibition of the Atg4B:LC3-AMC interaction (FIG. 9D). In contrast, the scrambled peptide showed no effect on protease activity.

SUPR 4B1W also showed an enhanced viability rescue phenotype (relative to SUPR 4B) in the DIRAS3 cell-based autophagy model (FIGS. 10A-C) as well as similar effects on p62 levels and LC3I/LC3II ratios. As expected, no viability effects were observed in normal cells at concentrations up to 50 μM. Chloroquine, on the other hand, resulted in a significant reduction in non-autophagic OVCAR8 viability at 48 hours which is consistent with non-specific toxicity reported elsewhere in the literature. A sequence-scrambled version of SUPR 4B1W showed no significant effect on normal or autophagic cells confirming that the biological effects of SUPR 4B1W are sequence-specific. Confocal microscopy experiments confirm the cell penetration of rhodamine-labeled SUPR 4B1W and suggest that it co-localizes with GFP-tagged LC3 (FIG. 11).

In order to test the effect of SUPR4B1W on cisplatin-resistant ovarian cancer cell lines, the OVCAR8 and Hey cell lines were treated with cisplatin (10 μM), combinations of cisplatin and SUPR peptide (50 M), or chloroquine (10 M) for 48 hr. MTT viability assays show that combinations of SUPR peptides with cisplatin re-sensitized the resistant cell lines to cisplatin, while scrambled versions of SUPR peptides had no effect (FIGS. 12A&C). Western blots show that cisplatin/SUPR peptide combinations dramatically perturbed LC3-I/LC3-II ratios and triggered accumulation of p62, suggesting inhibition of cisplatin-mediated autophagy (FIGS. 12B&D).

In animal model experiments, mice were implanted with a cisplatin-resistant ovarian cancer cell line (OVCAR8) and treated with carboplatin, SUPR4B1W peptide, or carboplatin+SUPR4B1W peptide for 4 weeks. At the conclusion of the study, the mice were sacrificed and the mass of the intraperitoneal tumors measured. Mice treated with peptide alone showed no change in tumor volume (FIG. 13). Mice treated with carboplatin alone showed the expected reduction in tumor volume. However, mice treated with both carboplatin and peptide were almost completely tumor-free (FIG. 13). Combining carboplatin and a scrambled, non-functional peptide showed no effect, indicating that the selected sequence is highly functional in vivo.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Birgisdottir, "The LIR motif—crucial for selective autophagy," *J. Cell Sci.*, 126:3237-3247, 2013.

Fiacco et al., "Directed evolution of scanning unnatural protease resistant (SUPR) peptides for in vivo applications," *Chembiochem.*, 17:1643-1651, 2016.

Kadowaki et al., "Nutrient control of macroautophagy in mammalian cells," *Mol. Aspects Med.*, 27:426-443, 2006.

Noda et al., "Atg8-family interacting motif crucial for selective autophagy," *FEBS Lett.*, 584:1379-1385, 2010.

Roberts & Szostak, "RNA-peptide fusions for the in vitro selection of peptides and proteins," *Proc. Natl. Acad. Sci. U.S.A.*, 94:12297-12302, 1997.

What is claimed is:

1. A cyclic peptide autophagy inhibitor comprising the peptide sequence of any one of SEQ ID NOs: 1-9, wherein the N-terminal amino group of the peptide is crosslinked to the side chain of the lysine residue at position 10.

2. The cyclic peptide of claim 1, wherein the N-terminal amino group of the peptide is crosslinked with the side chain of the lysine at position 10 using a di-succinimidyl glutarate crosslinker.

3. The cyclic peptide of claim 1, wherein the peptide comprises D amino acids.

4. The cyclic peptide of claim 1, wherein the peptide comprises at least one N-methylated amino acid.

5. The cyclic peptide of claim 1, wherein the peptide comprises at least one N-methylalanine.

6. The cyclic peptide of claim 5, wherein the amino acid in position 9 is an N-methylalanine.

7. The cyclic peptide of claim 1, wherein the peptide is lipidated.

8. The cyclic peptide of claim 1, wherein the peptide is PEG-ylated.

9. The cyclic peptide of claim 1, further comprising a detectable label.

10. A pharmaceutical formulation comprising a cyclic peptide of claim 1 in a pharmaceutically acceptable carrier.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)

<223> OTHER INFORMATION: Xaa can be any naturally occurring amino acid

<400> SEQUENCE: 1

Met Phe Pro His Arg Val Thr Ala Xaa Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Met Phe Ser His Arg Val Thr Leu Xaa Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Met Leu Ser Asp Ile Pro Val Asn Asp Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Met Tyr Ala Arg Ser Leu Arg Asp Xaa Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Met Asn Ala Arg Ser Leu Arg Asp Xaa Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:

```
<221> NAME/KEY: misc_feature
<222> LOCATION: (9)..(9)
<223> OTHER INFORMATION: Xaa can be any naturally occurring amino acid

<400> SEQUENCE: 6

Met Leu Ala Arg Ser Leu Arg Asp Xaa Lys
1               5               10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 7

Met Tyr Thr Arg Arg Val Arg Leu Xaa Lys
1               5               10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptie
<220> FEATURE:
<221> NAME/KEY: misc_feature
<222> LOCATION: (9)..(9)
<223> OTHER INFORMATION: Xaa can be any naturally occurring amino acid

<400> SEQUENCE: 8

Met Ser Leu His Arg Val Thr Val Xaa Lys
1               5               10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 9

Met Trp Pro His Arg Val Thr Ala Xaa Lys
1               5               10

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ala Leu Thr Trp Glu Glu Leu
1               5

<210> SEQ ID NO 11
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 11

Ser Gly Ser Trp Gln Ala Ile Gln Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Val Gly Asp Trp Glu Asp Leu Gln Asp
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Thr Leu Thr Tyr Asp Thr Leu Arg Phe
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Asp Asp Asp Trp Thr His Leu Ser Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ser Glu Asp Tyr Ile Ile Ile Leu Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 16

Met Xaa Xaa Xaa Arg Val Xaa Xaa Glx Lys
1               5                   10
```

-continued

```
<210> SEQ ID NO 17
<211> LENGTH: 10
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 17

Met Xaa Ala Arg Ser Leu Arg Asp Glx Lys
1               5                   10
```